(12) United States Patent
Boedicker et al.

(10) Patent No.: US 9,090,885 B2
(45) Date of Patent: Jul. 28, 2015

(54) CO-INCUBATING CONFINED MICROBIAL COMMUNITIES

(75) Inventors: James Q. Boedicker, Pasadena, CA (US); Rustem F. Ismagilov, Chicago, IL (US); Hyun Jung Kim, Brookline, MA (US)

(73) Assignee: The University of Chicago, Chicago, IL (US)

( * ) Notice: Subject to any disclaimer, the term of this patent is extended or adjusted under 35 U.S.C. 154(b) by 962 days.

(21) Appl. No.: 12/670,725

(22) PCT Filed: Jul. 28, 2008

(86) PCT No.: PCT/US2008/071370
§ 371 (c)(1),
(2), (4) Date: Jul. 21, 2010

(87) PCT Pub. No.: WO2009/015390
PCT Pub. Date: Jan. 29, 2009

(65) Prior Publication Data
US 2010/0317085 A1  Dec. 16, 2010

Related U.S. Application Data

(60) Provisional application No. 60/962,426, filed on Jul. 26, 2007, provisional application No. 61/052,490, filed on May 12, 2008.

(51) Int. Cl.
*C12Q 1/18* (2006.01)
*C12N 1/20* (2006.01)
*C12M 1/14* (2006.01)
*C12N 1/38* (2006.01)
*C12N 11/04* (2006.01)
*C12P 39/00* (2006.01)
*G01N 33/542* (2006.01)
*G01N 33/543* (2006.01)

(52) U.S. Cl.
CPC .. *C12N 1/20* (2013.01); *C12M 1/14* (2013.01); *C12N 1/38* (2013.01); *C12N 11/04* (2013.01); *C12P 39/00* (2013.01); *C12Q 1/18* (2013.01); *G01N 33/542* (2013.01); *G01N 33/54313* (2013.01)

(58) Field of Classification Search
None
See application file for complete search history.

(56) References Cited

U.S. PATENT DOCUMENTS

| | | | |
|---|---|---|---|
| 4,853,336 A | 8/1989 | Saros et al. | |
| 4,963,498 A | 10/1990 | Hillman et al. | |
| 5,185,099 A | 2/1993 | Delpuech et al. | |
| 5,725,853 A | 3/1998 | Dennis et al. | |
| 5,739,036 A | 4/1998 | Parris | |
| 5,872,010 A | 2/1999 | Karger et al. | |
| 5,997,636 A | 12/1999 | Gamarnik et al. | 117/70 |
| 6,130,098 A | 10/2000 | Handique et al. | |
| 6,140,053 A | 10/2000 | Köster | 435/6 |
| 6,180,372 B1 | 1/2001 | Franzen | 435/91.1 |
| 6,409,832 B2 | 6/2002 | Weigl et al. | |
| 6,451,610 B1 | 9/2002 | Gorman et al. | |
| 6,524,456 B1 | 2/2003 | Ramsey | |
| 6,544,568 B2 | 4/2003 | La Droitte et al. | |
| 6,569,631 B1 | 5/2003 | Pantoliano et al. | |
| 7,011,957 B2 * | 3/2006 | Lewis et al. | 435/34 |
| 7,129,091 B2 | 10/2006 | Ismagilov et al. | |
| 7,294,503 B2 | 11/2007 | Quake et al. | |
| 2001/0048900 A1 | 12/2001 | Bardell et al. | |
| 2002/0008029 A1 | 1/2002 | Williams et al. | 204/453 |
| 2002/0012971 A1 | 1/2002 | Mehta | 435/91.2 |
| 2002/0017464 A1 | 2/2002 | Parce et al. | 204/601 |
| 2002/0022261 A1 | 2/2002 | Anderson et al. | 435/287.2 |
| 2002/0058332 A1 | 5/2002 | Quake et al. | |
| 2002/0173033 A1 * | 11/2002 | Hammerick et al. | 435/305.2 |
| 2003/0064414 A1 | 4/2003 | Benecky et al. | |
| 2003/0229376 A1 | 12/2003 | Sandhu | |
| 2004/0005582 A1 | 1/2004 | Shipwash | |
| 2004/0037813 A1 | 2/2004 | Simpson et al. | |
| 2004/0072357 A1 | 4/2004 | Stiene et al. | |
| 2004/0181131 A1 | 9/2004 | Maynard et al. | |
| 2004/0224419 A1 | 11/2004 | Zheng et al. | 436/69 |
| 2005/0084923 A1 | 4/2005 | Mueller et al. | |
| 2006/0051329 A1 | 3/2006 | Lee et al. | |
| 2006/0078888 A1 | 4/2006 | Griffiths et al. | |
| 2006/0094119 A1 | 5/2006 | Ismagilov et al. | |
| 2006/0163385 A1 | 7/2006 | Link et al. | |
| 2007/0026439 A1 | 2/2007 | Faulstich et al. | |
| 2008/0003142 A1 | 1/2008 | Link et al. | |
| 2008/0014589 A1 | 1/2008 | Link et al. | |
| 2008/0124726 A1 | 5/2008 | Monforte | |
| 2009/0021728 A1 | 1/2009 | Heinz et al. | |

(Continued)

FOREIGN PATENT DOCUMENTS

| | | |
|---|---|---|
| CN | 2482070 | 3/2003 |
| EP | 0 816 837 A1 | 1/1998 |

(Continued)

OTHER PUBLICATIONS

Miller and Bassler, "Quorum Sensing in Bacteria," (2001), Annual Review of Microbiology, 55: 165-199.*

(Continued)

*Primary Examiner* — Jon P Weber
*Assistant Examiner* — Teresa E Knight
(74) *Attorney, Agent, or Firm* — Brinks Gilson & Lione

(57) ABSTRACT

This invention provides devices and methods that enable co-incubation of microorganisms. Also provided are methods of making such devices for co-incubation of microorganisms, and various applications of such devices.

12 Claims, 9 Drawing Sheets

(56) References Cited

U.S. PATENT DOCUMENTS

| | | |
|---|---|---|
| 2009/0060797 A1 | 3/2009 | Mathies et al. |
| 2009/0197248 A1 | 8/2009 | Griffiths et al. |
| 2010/0022414 A1 | 1/2010 | Link et al. |

FOREIGN PATENT DOCUMENTS

| | | |
|---|---|---|
| GB | 2097692 | 1/1981 |
| WO | WO 84/02000 | 5/1984 |
| WO | WO 97/29508 | 8/1997 |
| WO | WO 98/02237 | 1/1998 |
| WO | WO 98/52691 | 11/1998 |
| WO | WO 00/21666 | 4/2000 |
| WO | WO 01/77683 A1 | 10/2001 |
| WO | WO 02/12856 A1 | 2/2002 |
| WO | WO 02/23163 | 3/2002 |
| WO | WO 02/23163 A1 | 3/2002 |
| WO | WO 02/25243 A1 | 3/2002 |
| WO | WO 03/044221 A1 | 5/2003 |
| WO | WO 2004/038363 A2 | 5/2004 |
| WO | WO 2007/021343 A | 2/2007 |
| WO | WO 2007/021343 A2 | 2/2007 |
| WO | WO 2009/015390 A3 | 1/2009 |
| WO | WO 2009/048673 A3 | 4/2009 |

OTHER PUBLICATIONS

McDonald et al., "Fabrication of microfluidic systems in poly(dimethylsiloxane)," (2000), Electrophoresis, 21: 27-40.*

Bassler, "How bacteria talk to each other: regulation of gene expression by quorum sensing" (1999) vol. 2: 582-587.*

Gonzales et al. "Increased Growth of Microalga Chlorella vulgaris when Coimmobilized and Cocultured in Alginate Beads with the Plant-Growth-Promoting Bacterium Azospirillum basilense" (Apr. 2000) vol. 66, No. 4: 1527-1531.*

Abhyankar, Vinay V. et al., "Spatiotemporal Micropatterning of Cells on Arbitrary Substrates", *Analytical Chemistry*, vol. 79, No. 11, 2007, pp. 4066-4073.

Abrams, William R. et al., "Development of a Microfluidic Device for Detection of Pathogens in Oral Samples Using Upconverting Phosphor Technology (UPT)", *Annals of the New York Academy of Sciences*, 1098, 2007, 375-388.

Adamson, David N. et al., "Production of arrays of chemically distinct nanolitre plugs via repeated splitting in microfluidic devices", *Lab Chip*, vol. 6, 2006, pp. 1178-1186.

Adler, Michael et al., "Sensitivity by combination: immune-PCR and related technologies", *Analyst*, vol. 133, 2008, pp. 702-718.

Aharoni, Amir et al., "High-Throughput Screening of Enzyme Libraries: Thiolactonases Evolved by Fluorescence-Activated Sorting of Single Cells in Emulsion Compartments", *Chemistry & Biology*, vol. 12, 2005, pp. 1281-1289.

Ahn, Keunho et al., "Dielectrophoretic manipulation of drops for high-speed microfluidic sorting devices", *Applied Physics Letters* 88, 024104 (2006).

Akselband, Y. et al., "Rapid mycobacteria drug susceptibility testing using Gel Microdrop (GMD) Growth Assay and flow cytometry", *Journal of Microbiological Methods*, 62, 2005, pp. 181-197.

Allison, Steven D., "Cheaters, diffusion and nutrients constrain decomposition by microbial enzymes in spatially structured environments", *Ecology Letters*, (2005) vol. 8, pp. 626-635.

Almeida, P.F., "Selection and Application of Microorganisms to Improve Oil Recovery", *Eng. Life Sci.*, 2004, 4, No. 4, pp. 319-325.

Anderson, Janelle R., "Fabrication of Topologically Complex Three-Dimensional Microfluidic Systems in PDMS by Rapid Prototyping", *Analytical Chemistry*, vol. 72, No. 1, Jul. 15, 2000, pp. 3158-3164.

Baker, Carolyn N. et al., "Evaluation of Alamar Colorimetric Broth Microdilution Susceptibility Testing Method for Staphylococci and Enterococci", *Journal of Clinical Microbiology*, Nov. 1996, vol. 34, No. 11, pp. 2654-2659.

Balagadde, Frederick K. et al., "Long-Term Monitoring of Bacteria Undergoing Programmed Population Control in a Microchemostat", *Science*, vol. 309, 2005, pp. 137-140.

Ball, Robert et al., "Cmatrix: Software for Physiologically Based Pharmacokinetic Modeling Using a Symbolic Matrix Representation System", *Comput. Biol. Med.*, vol. 24, No. 4, pp. 269-276, 1994.

Bianchi, Diana W. et al., "Isolation of fetal DNA from nucleated erythrocytes in maternal blood", *Proc. Natl. Acad. Sci. USA*, vol. 87, pp. 3279-3283, May 1990.

Boccazzi, Paolo et al., "Gene expression analysis of *Escherichia coli* grown in miniaturized bioreactor platforms for high-throughput analysis of growth and genomic data", *Appl Microbiol Biotechnol*, 2005, vol. 68, pp. 518-532.

Bode, Helge Björn et al., "Big Effects from Small Changes: Possible Ways to Explore Nature's Chemical Diversity", *ChemBioChem*, 2002, vol. 3, pp. 619-627.

Brenner, Katie et al., "Engineered bidirectional communication mediates a consensus in a Mpp icrobial biofilm consortium", 17300-17204, PNAS, Oct. 29, 2007 vol. 104, No. 44.

Buckpitt, Alan R. et al., "Hepatic and Pulmonary Microsomal Metabolism of Naphthalene to Glutathione Adducts: Factors Affecting the Relative Rates of Conjugate Formation", *The Journal of Pharmacology and Experimental Therapeutics*, vol. 231, No. 2, 1984, pp. 291-300.

Carrigan, Shawn D. et al., "Toward Resolving the Challenges of Sepsis Diagnosis", *Clinical Chemistry*, 50:8, 2004, pp. 1301-1314.

Chabert, Max et al., "Microfluidic high-throughput encapsulation and hydrodynamic self-sorting of single cells", *PNAS*, Mar. 4, 2008, vol. 105, No. 9, pp. 3191-3196.

Chayen, Naomi E., "Crystallization with oils: a new dimension in macromolecular crystal growth", *Journal of Crystal Growth*, vol. 196, 1999, pp. 434-441.

Chen, Delai L. et al., "Microfluidic cartridges preloaded with nanoliter plugs of reagents: an alternative to 96-well plates for screening", *Current Opinion in Chemical Biology*, 2006, 10:226-231.

Cheung, Yuk Kee et al., "Direct patterning of composite biocompatible microstructures using microfluidics", *Lab Chip*, 2007, 7, pp. 574-579.

Chiu, Daniel T. et al., "Chemical Transformations in Individual Ultrasmall Biomimetic Containers", *Science*, vol. 283, Mar. 19, 1999, pp. 1892-1895.

Chueh, Bor-han et al., "Leakage-Free Bonding of Porous Membranes into Layered Microfluidic Array Systems", *Analytical Chemistry*, vol. 79, No. 9, May 1, 2007, pp. 3504-3508.

Weijia, Xu et al., "CN2482070Y: Blood coagulation promoting ball", Abstract, published Mar. 13, 2002, Application CN20010001211231U.

Cowen, Leah E. et al., "Hsp90 Potentiates the Rapid Evolution of New Traits: Drug Resistance in Diverse Fungi", *Science*, vol. 309, Sep. 30, 2005, pp. 2185-2188.

Daniilidis, Angelos et al., "Fatal cells in maternal circulation—potentials for prenatal control", *Journal of Biological Research* 6: 119-130, 2006.

Dateo, Christopher E. et al., "Bistability and Oscillations in the Autocatalytic Chlorite-Iodide Reaction in a Stirred-Flow Reactor", *J. Am. Chem. Soc.*, 1982, vol. 104, pp. 504-509.

De-Bashan, Luz E. et al., "Removal of ammonium and phosphorus ions from synthetic wastewater by the microalgae *Chlorella vulgaris* coimmobilized in alginate beads with the microalgae growth-promoting bacterium *Azospirillum brasilense*", *Water Research*, vol. 36, No. 12, Jul. 1, 2002, pp. 2941-2948.

Dechesne, Arnaud et al., "Limited diffusive fluxes of substrate facilitate coexistence of two competing bacterial strains", *FEMS Microbiol. Ecol.*, vol. 64, 2008, pp. 1-8.

Degenkolb, Thomas et al., "Formation of New Lipoaminopeptides, Acremostatins A, B, and C, by Co-cultivation of *Acremonium* sp. Tbp-5 and *Mycogene rosea* DSM 12973", *Bisci. Biotechnol. Biochem.*, vol. 66, No. 4, 2002, pp. 883-886.

DelRaso, N.J., "In vitro methodologies for enhanced toxicity testing", *Toxicology Letters*, vol. 68, 1993, pp. 91-99.

Dendukuri, Dhananjay et al., "Continuous-flow lithography for high-throughput microparticle synthesis", *Nature Materials*, vol. 5, May 2006, pp. 365-369.

(56) References Cited

OTHER PUBLICATIONS

Du, Wen-Bin et al., "High-Throughput Nanoliter Sample Introduction Microfluidic Chip-Based Flow Injection Analysis System with Gravity-Driven Flows", *Analytical Chemistry*, vol. 77, No. 5, Mar. 1, 2005, pp. 1330-1337.

Easley, Christopher J. et al., "On-chip pressure injection for integration of infrared-mediated DNA amplification with electrophoretic separation", *Lab Chip*, 2006, vol. 6, pp. 601-610.

Tanaka, H. et al., "Ethanol production from startch by a coimmobilized mixed culture system of *Aspergillus awamoria* and *Zymomonas mobilis*", *Biotechnology and Bioengineering*, vol. 28, No. 12, Dec. 1986, pp. 1761-1768.

Titomanlio et al., Capillary experiments of flow induced crystallization of HDPE:, *AlChe Journal*, 1990, vol. 36, No. 1, pp. 13-18.

Edwards, Katie A. et al., "Liposomes in analyses", *Talanta*, vol. 68, 2006, pp. 1421-1431.

El-Ali, Jamil et al., "Cell Stimulus and Lysis in a Microfluidic Device with Segmented Gas-Liquid Flow", *Anal. Chem.*, vol. 77, No. 11, Jun. 1, 2005, pp. 3629-3636.

Endo, Masatoshi et al., "Kinetic determination of trace cobalt(II) by visual autocatalytic indication", *Talanta*, vol. 47, 1998, pp. 349-353.

Endo, Masatoshi et al., "Autocatalytic Decomposition of Cobalt Complexes as an Indicator System for the Determination of Trace Amounts of Cobalt and Effectors", *Analyst*, Apr. 1996, vol. 121, pp. 391-394.

Farr, Bary M., "Prevention and control of methicillin-resistant *Staphylococcus aureus* infections", University of Virginia, *Current Opinion in Infectious Diseases*, 2004, vol. 17, pp. 317-322.

Fernandez-Lafuente, Roberto et al., "Immobilization of lipases by selective adsorption on hydrophobic supports", *Chemistry and Physics of Lipids*, vol. 93, 1998, pp. 185-197.

Ferrari, Belinda C. et al., "Microcolony Cultivation on a Soil Substrate Membrane System Selects for Previously Uncultured Soil Bacteria", *Applied and Environmental Microbiology*, Dec. 2005, vol. 71, No. 12, pp. 8714-8720.

Fialkowski, Marcin et al., "Self-assembly of polymeric microspheres of complex internal structures", Nature Materials, vol. 4, Jan. 2005, www.nature.com/naturematerials.

Francis, Karl et al., "Effective intercelular communication distances are determined by the relative time constants for cyto/chemokine secretion and diffusion", *Proc. Natl. Acad. Sci. USA*, Nov. 1997, vol. 94, pp. 12258-12263.

Franzblau, Scott G. et al., "Rapid, Low-Technology MIC Determination with Clinical *Mycobacterium tuberculosusis*, Isolates by Using the Microplate Alamar Blue Assay", *Journal of Clinical Microbiology*, Feb. 1998, vol. 36, No. 2, pp. 362-366.

Fridkin, Scott K. et al., "Antimicrobial Resistance Prevalence Rates in Hospital Antibiograms Reflect Prevalence Rates among Pathogens Associated with Hospital-Acquired Infections", *Cumulative Susceptibility Data*, CID 2001:33 (Aug. 1), pp. 324-329.

Gailani, David et al., "Factor XI Activation in a Revised Model of Blood Coagulation", *Science*, New Series, vol. 253, No. 5022, Aug. 23, 1991, pp. 909-912.

Garcia-Ruiz, J. M. et al., "Investigations on Protein Crystal Growth by the Gel Acupuncture Method", *Acta Cryst.*, 1994, D50, pp. 484-490.

Garcia-Ruiz, Juan Ma. et al., "A supersaturation wave of protein crystallization", *Journal of Crystal Growth*, vol. 232, 2001, pp. 149-155.

Stewart, Patrick Douglas Shaw, "Combining chemical reagents", UK Patent Application, GB 2097692A.

Glotzer, Sharon C. et al., "Anisotropy of building blocks and their assembly into complex structures", *Nature Materials*, vol. 6, Aug. 2007, www.nature.com/naturematerials.

Gonzalez-Pastor et al., "Cannibalism by Sporulating Bacteria", *Science*, New Series, vol. 301, No. 5632, Jul. 25, 2003, pp. 510-513.

Goodall, Jennifer L. et al., "Operation of Mixed-Culture Immobilized Cell Reactors for the Metabolism of Meta- and Para-Nitrobenzoate by *Comamonas* Sp. JS46 and *Comamonas* Sp. J547", *Biotechnology and Bioengineering*, vol. 59, No. 1, Jul. 5, 1998, pp. 21-27.

Gorris, Hans H. et al., "Stochastic inhibitor release and binding from single-enzyme molecules", *PNAS*, Nov. 6, 2007, vol. 104, No. 45, pp. 17680-17685.

Green, David W. et al., "Biomineralized Polysaccharide Capsules for Encapsulation, Organization, and Delivery of Human Cell Types and Growth Factors", *Advanced Functional Materials*, 2005, vol. 15, pp. 917-923.

Grodrian, Andreas et al., "Segmented flow generation by chip reactors for highly parallelized cell cultivation", *Biosensors and Bioelectronics*, vol. 19, 2004, pp. 1421-1428.

Groisman, Alex et al., "A microfluidic chemostat for experiments with bacterial and yeast cells", *Nature Methods*, vol. 2, No. 9, Sep. 2005, pp. 685-689.

Grundmann, G. L. et al., "Spatial Modeling of Nitrifier Microhabitats in Soil", *Soil Sci. Soc. Am. J.*, vol. 65, Nov.-Dec. 2001, pp. 1709-1716.

Gulliksen, Anja et al., "Parallel nanoliter detection of cancer markers using polymer microchips", *Lab Chip*, 2005, vol. 5, pp. 416-420.

Haddad, Sami et al., "A methodology for solving physiologically based pharmacokinetic models without the use of simulation softwares", *Toxicology Letters*, vol. 85, 1996, pp. 113-126.

Haies, Donald M. et al., "Morphometric Study of Rat Lung Cells", *The American review of respiratory disease*, vol. 123, No. 5, 1981, pp. 533-541.

Hansen, Susse Kirkelund et al., "Evolution of species interactions in a biofilm community", *Nature*, vol. 445, Feb. 1, 2007, pp. 533-536.

Massell, Michael P. et al., "Species coexistence and self-organizing spatial dynamics", *Nature*, vol. 370, Jul. 28, 1994, pp. 290-292.

He, Mingyan et al., "Selective Encapsulation of Single Cells and Subcellular Organelles into Picoliter- and Femtoliter-Volume Droplets", *Anal. Chem.*, 2005, vol. 77, pp. 1539-1544.

Ho, Chi-Chih et al., "Novel Fabrication of Janus Particles from the Surfaces of Electrospun Polymer Fibers", *Langmuir*, vol. 24, No. 11, 2008, pp. 5663-5666.

Hoang, Kim-Chi T., "Physiologically based pharmacokinetic models: mathematical fundamentals and simulation implementations", *Toxicology Letters*, vol. 79, 1995, pp. 99-106.

Hodgson, John, "ADMET-turning chemicals into drugs", *Nature Biotechnology*, vol. 19, Aug. 2001, pp. 722-726, http://biotech.nature.com.

Hong, Jong Wook et al., "A nanoliter-scale nucleic acid processor with parallel architecture", *Nature Biotechnology*, vol. 22, No. 4, Apr. 2004, pp. 435-439.

Horvat, Rebecca T. et al., "Effect of Duplicate Isolates of Methicillin-Susceptible and Methicillin-Resistant *Staphylococcus aureus* on Antibiogram Data", *Journal of Clinical Microbiology*, vol. 41, No. 10, Oct. 2003, pp. 4611-4616.

Horvath, Attila K. et al., "Kinetics and Mechanism of the Chlorine Dioxide-Tetrathionate Reaction", *J. Phys. Chem. A*, 2003, vol. 107, pp. 10063-10068.

Horvath, Attila K. et al., "Oscillatory Photochemical Decomposition of Tetrathionate Ion", *J. Am. Chem. Soc.*, 2002, vol. 124, No. 37, pp. 10956-10957.

Huang, Jing et al., "A Yeast Genetic System for Selecting Small Molecule Inhibitors of Protein-Protein Interactions in Nanodroplets", *Proc. Natl. Acad. Sci. USA*, vol. 94, 1997, pp. 13396-13401.

Huang, Bo et al., "Counting Low-Copy Number Proteins in a Single Cell", *Science*, vol. 315, No. 81, 2007, pp. 81-84.

Huebner, A. et al., "Quantitative detection of protein expression in single cells using droplet microfluidics", *Chem. Commun.*, 2007, pp. 1218-1220, www.rsc.org/chemcom.

Huh, Dongeun et al., "Gravity-Driven Microfluidic Particle Sorting Device with Hydrodynamic Separation Amplification", Anal. Chem., vol. 79, No. 4, Feb. 15, 2007, pp. 1369-1376.

Hunfeld, K. P., "SeptiFast: A new real-time PCR-based assay for rapid molecular detection of pathogens in patients with clinical sepsis", *International Journal of Medical Microbiology*, vol. 297, 2007, p. 32.

(56) References Cited

OTHER PUBLICATIONS

Hwang, Paul M. et al., "Ferredoxin reductase affects p53-dependent, 5-fluorouracil-induced apoptosis in colorectal cancer cells", *Nature Medicine*, vol. 7, No. 10, Oct. 2001, pp. 1111-1117.
Ichimura, Kunihiro, "Nonlinear Organic Reactions to Proliferate Acidic and Basic Molecules and Their Applications", *The Chemical Record*, vol. 2, 2002, pp. 46-55.
Ikeda, Kazumasa et al., "Bioactivation of Tegafur to 5-Fluorouracil Is Catalyzed by Cytochrome P-450 2A6 in Human Liver Microsomes in Vitro", *Clinical Cancer Research*, vol. 6, Nov. 2000, pp. 4409-4415.
Ingham, Colin J. et al., "The micro-Petri dish, a million-well growth chip for the culture and high-throughput screening of microorganisms", *PNAS*, Nov. 13, 2007, vol. 104, No. 46, pp. 18217-18222.
Ismagilov, Rustem F. et al., "Microfluidic Arrays of Fluid—Fluid Diffusional Contacts as Detection Elements and Combinatorial Tools", *Anal. Chem.*, vol. 73, No. 21, Nov. 1, 2007, pp. 5207-5213.
Ezaki, Masami et al., "Biphenomycin A Production by a Mixed Culture", *Appl. Environ. Microbiol.*, vol. 58, No. 12, 1992, pp. 3879-3882.
Jain, Rakesh Kumar et al., "Microbial diversity: Application of micro-organisms for the biodegradation of xenobiotics", *Current Science*, vol. 89, No. 1, Jul. 10, 2005, pp. 101-112.
Jang, Ji-Hyun et al., "A Route to Three-Dimensional Structures in a Microfluidic Device: Stop- Flow Interference Lithography", *Angew. Chem. Int. Ed.*, vol. 46, 2007, pp. 9027-9031.
Jiang, Yanjun et al., "Fabrication of Polysaccharide-inorganic Hybrid Biocapsules with Improved Catalytic Activity and Stability", *Ind. Eng. Chem. Res.*, vol. 47, No. 8, 2008, pp. 2495-2501.
Li, Liang et al., "Nanoliter microfluidic hybrid method for simultaneous screening and optimization validated with crtystallization of membrane proteins", *Proceedings of the National Academy of Sciences of the United States of America* (PNAS), vol. 103, No. 51, Dec. 19, 2006, pp. 19243-19248.
Kastrup, Christian J. et al., "Modular chemical mechanism predicts spatiotemporal dynamics of initiation in the complex network of hemostasis", *Proceedings of the National Academy of Sciences of the United States of America* (PNAS), vol. 103, No. 43, Oct. 24, 2006, pp. 15747-15752.
Keymer, Juan E. et al, "Bacterial Metapopulations in Nanofabridcated Landscapes", *Proceedings of the National Academy of Sciences of the United States of America* (PNAS), vol. 103, No. 46, Nov. 14, 2006, pp. 17290-17295.
Swenson, William et al., "Artificial Ecosystem Selection", *Proceedings of the National Academy of Sciences of the United States of America* (PNAS), vol. 97, No. 16, Aug. 1, 2000, pp. 9110-9114.
Williams, Hywel T.P. et al., "Artificial selection of simulated microbial ecosystems", *Proceedings of the National Academy of Sciences of the United States of America* (PNAS), vol. 104, No. 21, May 22, 2007, pp. 8918-8923.
Wang, Lei et al., "Evolution of New Nonantibody Proteins via Iterative Somatic Hypermutation", *Proceedings of the National Academy of Sciences of the United States of America* (PNAS), vol. 101, No. 48, Nov. 30, 2004, pp. 16745-16749.
Zengler, Karsten et al., "Cultivating the Uncultured", *Proceedings of the National Academy of Sciences of the United States of America* (PNAS), vol. 99, No. 24, Nov. 26, 2002, pp. 15681-15686.
Miller, Oliver J. et al., "Directed evolution by in vitro compartmentalization", *Nature Methods*, vol. 3, No. 7, Jul. 2006, pp. 561-570.
Leamon, John H. et al., "Overview: methods and applications for droplet compartmentalization", *Nature Methods*, vol., 3, No. 7, Jul. 2006, pp. 541-543.
Poulin, Patrick et al., "A Priori Prediction of Tissue: Plasma Partition Coefficients of Drugs to Facilitate the Use of Physiologically-Based Pharmacokinetic Models in Drug Discovery", *Journal of Pharmaceutical Sciences*, vol. 89, No. 1, Jan. 2000, pp. 16-35.
Nielsen, Alex T. et al., "Role of commensal relationships on the spatial structure of a surface-attached microbial consortium", *Environmental Microbiology*, 2(1), 2000, pp. 59-68.

Nguyen, H. Bryant et al., "Severe Sepsis and Septic Shock: Review of the Literature and Emergency Department Management Guidelines", *Annals of Emergency Medicine*, vol. 48, No. I, Jul. 2006, pp. 28-54.e1.
Naito, Koji et al., "Activation of Human Blood Coagulation Factor XI Independent of Factor XII", *The Journal of Biological Chemistry*, vol. 266, No. 12, Apr. 25, 1991, pp. 7353-7358.
Kastrup, Christian J. et al., "Using Chemistry and Microfluidics to Understand the Spatial Dynamics of Complex Biological Networks", *Accounts of Chemical Research*, vol. 41, No. 4, Apr. 2008, pp. 549-558.
Koh, Chee G. et al., "Integrating Polymerase Chain Reaction, Valving, and Electrophoresis in a Plastic Device for Bacterial Detection", *Analytical Chemistry*, vol. 75, No. 17, Sep. 1, 2003, pp. 4591-4598.
Kuharsky, Andrew L. et al., "Surface-Mediated Control of Blood Coagulation: The Role of Binding Site Densities and Platelet Deposition", *Biophysical Journal*, vol. 80, Mar. 2001, pp. 1050-1074.
Kawabata, Shun-ichiro et al., "Highly sensitive peptide-4-methylcoumaryl-7-amide substrates for blood-clotting proteases and trypsin", *European Journal of Biochemistry*, vol. 172, Feb. 1988, pp. 17-25.
Nagypál, István et al., "Fluctuations and Stirring Rate Effects in the Chlorite-Thiosulfate Reaction", *The Journal of Physical Chemistry*, vol. 90, No. 23, 1986, pp. 6285-6292.
Martin, Anandi et al., "Resazurin Microtiter Assay Plate Testing of *Mycobacterium tuberculosis* Susceptibilities to Second-Line Drugs: Rapid, Simple, and Inexpensive Method", *Antimicrobial Agents and Chemotherapy*, vol. 47, No. 11, Nov. 2003, pp. 3616-3619.
Martin, Greg S. et al., "The Epidemiology of Sepsis in the United States from 1979-2000", *The New England Journal of Medicine*, vol. 348, No. 16, Apr. 17, 2003, pp. 1546-1554.
Moran, Gregory J. et al., "Methicillin-Resistant *S. aureus* Infections among Patients in the Emergency Department", *The New England Journal of Medicine*, vol. 355, No. 7, Aug. 17, 2006, pp. 666-674.
Murakami, Kazuhisa et al., "Identification of Methicillin-Resistant Strains of Staphylococci by Polymerase Chain Reaction", *Journal of Clinical Microbiology*, vol. 29, No. 10, Oct. 1991, pp. 2240-2244.
Mountzouros, Kenneth T. et al., "Detection of Complement-Mediated Antibody-Dependent Bactericidal Activity in a Fluorescence-Based Serum Bactericidal Assay for Group B *Neisseria meningitidis*", *Journal of Clinical Microbiology*, vol. 38, No. 8, Aug. 2000, pp. 2878-2884.
Poppert, Sven et al., "Rapid Diagnosis of Bacterial Meningitis by Real-Time PCR and Fluorescence In Situ Hybridization," *Journal of Clinical Microbiology*, vol. 43, No. 7, Jul. 2005, pp. 3390-3397.
Ryan, Colleen et al., "Rapid Assay for Mycobacterial Growth and Antibiotic Susceptibility Using Gel Microdrop Encapsulation", *Journal of Clinical Microbiology*, vol. 33, No. 7, Jul. 1995, pp. 1720-1726.
Kato, Souichiro et al., "Stable Coexistence of Five Bacterial Strains as a Cellose-Degrading Community", *Applied and Environmental Microbiology*, vol. 71, No. 11, Nov. 2005, pp. 7099-7106.
Rabaey, Korneel et al., "Biofuel Cells Select for Microbial Consortia That Self-Mediate Electron Transfer", *Applied and Environmental Microbiology*, vol. 70, No. 9, Sep. 2004, pp. 5373-5382.
Louvain-Quintard, Virginie B. et al., "Thrombin-activable Factor X Re-establishes an Intrinisic Amplificaion in Tenase-deficient Plasmas", *The Journal of Biological Chemistry*, vol. 280, No. 50, Dec. 16, 2005, pp. 41352-41359.
Love, J. Christopher et al., "A microengraving method for rapid selection of single cells producing antigen-specific antibodies", *Nature Biotechnology*, vol. 24, No. 6, Jun. 2006, pp. 703-707.
Seong, Gi Hun et al., "Fabrication of Microchambers Defined by Photopolymerized Hydrogels and Weirs within Microfluidic Systems: Application to DNA Hybridization", *Analytical Chemistry*, vol. 74, No. 14, Jul. 15, 2002, pp. 3372-3377.
Song, Helen et al., "On-Chip Titration of an Anticoagulant Argatroban and Determination of the Clotting Time within Whole Blood or Plasma Using a Plug-Based Microfluidic System", *Analytical Chemistry*, vol. 78, No. 14, Jul. 15, 2006, pp. 4839-4849.
Whitaker, Ragnhild D. et al., "Multianalyte Single-Cell Analysis with Multiple Cell Lines Using a Fiber-Optic Array", *Analytical Chemistry*, vol. 79, No. 23, Dec. 1, 2007, pp. 9045-9053.

(56) References Cited

OTHER PUBLICATIONS

Stone, Stuart R. et al., "Kinetics of the Inhibition of Thrombin by Hirudin", *Biochemistry*, vol. 25, No. 16, 1986, pp. 4622-4628.

Swenson, William et al., "Artificial selection of microbial ecosystems for 3-chloroaniline biodegradation", *Environmental Microbiology*, vol. 2, No. 5, 2000, pp. 564-571.

Roach, L. Spencer et al., "Controlling Nonspecific Protein Adsorption in a Plug-Based Microfluidic System by Controlling Interfacial Chemistry Using Fluorous-Phase Surfactants", *Analytical Chemistry*, vol. 77, No. 3, Feb. 1, 2005, pp. 785-796.

Wong, Pak Kin et al., "Electrokinetic Bioprocessor for Concentrating Cells and Molecules", *Analytical Chemistry*, vol. 76, No. 23, Dec. 1, 2004, pp. 6908-6914.

Yuan, Ling et al., "Laboratory-Directed Protein Evolution", *Microbiology and Molecular Biology Reviews*, vol. 69, No. 3, Sep. 2005, pp. 373-392.

Komatsu, Tomoko et al., "Roles of Cytochromes P4450, 1A2, 2A6, and 2C8 in 5-Fluorouracil Formation From Tegafur, An Anticancer Prodrug, In Human Liver Microsomes", *Drug Metabolism and Disposition*, vol. 28, No. 12, pp. 1457-1463.

Yamazaki, Hiroshi et al., Rat Cytochrome P450 1A and 3A Enzymes Involved in Bioactivation of Tegafur to 5-Fluorouracil and Autoinduced by Tegafur in Liver Microsomes, *Drug Metabolism and Disposition*, vol. 29, No. 6, pp. 794-797.

Takeuchi, Shoji et al., "Controlling the Shape of Filamentous Cells of *Escherichia coli*", *Nano Lett.*, vol. 5, No. 9, 2005, pp. 1819-1823.

Ohno, Michiyo et al., "Establishing the Independent Culture of a Strictly Symbiotic Bacterium Symbiobacterium thermophilum from Its Supporting *Bacillus* Strain", *Biosci. Biotechnol. Biochem.*, vol. 63, No. 6, 1999, pp. 1083-1090.

Reimer, Larry G. et al., "Update on Detection of Bacteremia and Fungemia", *Clinical Microbiology Reviews*, vol. 10, No. 3, Jul. 1997, pp. 444-465.

Roth, Robert I. et al., "Lipopolysaccharide-Binding Proteins of *Limulus* Amebocyte Lysate", *Infection and Immunity*, vol. 61, No. 3, Mar. 1993, pp. 1033-1039.

Zheng, Gengfeng et al., "Multiplexed electrical detection of cancer markers with nanowire sensor arrays", *Nature Biotechnology*, vol. 23, No. 10, Oct. 2005, pp. 1294-1301.

Kaltsas, P. et al., "Development of a time-to-positivity assay as a tool in the antibiotic management of septic patients", *Clinical Microbiology and Infection*, vol. 11, No. 2, Feb. 2005, pp. 109-114.

Kerr, Benjamin et al., "Local dispersal promotes biodiversity in a real-life game of rock-paper-scissors", *Nature*, vol. 418, Jul. 11, 2002, pp. 171-174.

Shepherd, Robert F. et al., "Microfluidic Assembly of Homogeneous and Janus Colloid-Filled Hydrogel Granules", *Langmuir*, vol. 22, No. 21, 2006, pp. 8618-8622.

Shintaku, Hirofumi et al., "Micro cell encapsulation and its hydrogel-beads production using microfluidic device", *Microsyst Technol*, vol. 13, 2007, pp. 951-958.

Slattery, M. et al., "Competition-Mediated Antibiotic Induction in the Marine Bacterium *Streptomyces tenjimariensis*", *Microbial Ecology*, vol. 41, No. 2, Feb. 2001, pp. 90-96.

Slob, W. et al., "Structural Identifiability of PBPK Models: Practical Consequences for Modeling Strategies and Study Designs", *Critical Reviews in Toxicology*, vol. 27, No. 3, 1997, pp. 261-272.

Smyth, Paul G. et al., "Markers of Apoptosis: Methods for Elucidating the Mechanism of Apoptotic Cell Death from the Nervous System", *BioTechniques*, vol. 32, No. 3, Mar. 2002, pp. 648-665.

Song, Simon et al., "On-chip sample preconcentration for integrated microfluidic analysis", *Anal Bioanal Chem*, vol. 384, 2006, pp. 41-43.

Song, Helen et al., "Reactions in Droplets in Microfluidic Channels", *Angew. Chem. Int. Ed.*, vol. 45, 2006, pp. 7336-7356, www.angewandte.org.

Song, Helen et al., "A Microfluidic System for Controlling Reaction Networks in Time", *Angew. Chem. Int. Ed.*, vol. 42, No. 7, 2003, pp. 767-772.

Sugiura, Shinji et al., "Interfacial Tension Driven Monodispersed Droplet Formation from Microfabricated Channel Array", *Langmuir*, vol. 17, No. 18, 2001, pp. 5562-5566.

Sweeney, L. M. et al., "A Cell Culture Analogue of Rodent Physiology: Application to Naphthalene Toxicology", *Toxic in Vitro*, vol. 9, No. 3, 1995, pp. 307-316.

Tan, Yung-Chieh et al., "Microfluidic sorting of droplets by size", *Microfluid Nanofluid*, vol. 4, 2008, pp. 343-348.

Tankersley, Donald L. et al., "Kinetics of Activation and Autoactivation of Human Factor XII", *Biochemistry*, vol. 23, No. 2, 1984, pp. 273-279.

Torkkeli, Altti et al., "Droplet Manipulation on a Superhydrophobic Surface for Microchemical Analysis", *The 11th International Conference on Solid-State Sensors and Actuators*, Munich, Germany, Jun. 10-14, 2001, XP-002236824.

Treves, D. S. et al., "A Two-Species Test of the Hypothesis That Spatial Isolation Influences Microbial Diversity in Soil", *Microbial Ecology*, vol. 45, 2003, pp. 20-28.

Tsuji, Brian T. et al., "Community- and health care-associated methicillin-resistant *Staphylococcus aureus*: a comparison of molecular epidemiology and antimicrobial activities of various agents", *Diagnostic Microbiology and Infectious Disease*, vol. 58, 2007, pp. 41-47.

Tsukada, Shigeharu et al., "Chemiluminescence from fluorescent organic compounds induced by cobalt(II) catalyzed decomposition of peroxomonosulfate", *Analytica Chimica Acta*, vol. 371, 1998, pp. 163-170.

Ulmer, Jana S. et al., "Ecotin is a potent inhibitor of the contact system proteases factor XIIa and plasma kallikrein", *FEBS Letters*, vol. 365, 1995, pp. 159-163.

Weibel, Douglas B. et al., "Microfabrication meets microbiology", *Nature Reviews/Microbiology*, vol. 5, Mar. 2007, pp. 209-218, www.nature.com/reviews/micro.

Utada, A. S. et al., "Monodisperse Double Emulsions Generated from a Microcapillary Device", *Science*, vol. 308, Apr. 22, 2005, pp. 537-541, www.sciencemag.org.

Vliegen, Inge et al., "Rapid identification of bacteria by real-time amplification and sequencing of the 16S rRNA gene", *Journal of Microbiological Methods*, vol. 66, 2006, pp. 156-164; www.sciencedirect.com.

Walther, Andreas et al., "Emulsion Polymerization Using Janus Particles as Stabilizers", *Angew. Chem. Int. Ed.*, vol. 47, 2008, pp. 711-714, www.angewandte.org.

Wang, Chaoyang et al., "Facile Fabrication of Hybrid Colloidosomes with Alginate Gel Cores and Shells of Porous $CaCO_3$ Microparticles", *ChemPhysChem*, vol. 8, 2007, pp. 1157-1160, www.chemphyschem.org.

Xia, Younan et al., "Soft Lithography", *Annu. Rev. Mater. Sci.*, vol. 28, 1998, pp. 153-184.

Yang, Jianing et al., "High sensitivity PCR assay in plastic micro reactors", *Lab Chip*, vol. 2, 2002, pp. 179-187.

Young, I. M. et al., "Interactions and Self-Organization in the Soil-Microbe Complex", *Science*, New Series, vol. 304, No. 5677, Jun. 11, 2004, pp. 1634-1637.

Yu, Ji et al., "Probing Gene Expression in Live Cells, One Protein Molecule at a Time", *Science*, vol. 311, Mar. 17, 2006, pp. 1600-1603, www.sicencemag.org.

Yu, Hongmei et al., "Understanding microchannel culture: parameters involved in soluble factor signaling", *Lab Chip*, vol. 7, 2007, pp. 726-730, www.rsc.org/loc.

Zhu, Lei et al., "Signal Amplification by Allosteric Catalysis", *Angew. Chem. Int. Ed.*, vol. 45, 2006, pp. 1190-1196, www.angewandte.org.

Scruggs, Allan Wallace et al., "Optical Processing of Bacterial Libraries for Directed Evolution", *Biotechnology and Bioengineering*, vol. 84, No. 4, Nov. 20, 2003, pp. 445-451.

Seong, Gi Hun et al., "Efficient Mixing and Reactions within Microfluidic Channels Using Microbead-Supported Catalysts", *J. Am. Chem. Soc.*, vol. 124, 2002, pp. 13360-13361.

Runyon, Matthew K. et al., "Minimal Functional Model of Hemostasis in a Biomimetic Microfluidic System", *Angew. Chem. Int. Ed.*, vol. 43, 2004, pp. 1531-1536, www.angewandte.org.

(56) References Cited

OTHER PUBLICATIONS

Price-Whelan, Alexa et al., "Rethinking 'secondary' metabolism: physiological roles for phenazine antibiotics", *Nature Chemical Biology*, vol. 2, No. 2, Feb. 2006, pp. 71-78.
Patel, Dipak et al., "Continuous affinity-based selection: rapid screening and simultaneous amplification of bacterial surface-display libraries", *Biochem J.*, vol. 357, 2001, pp. 779-785.
Ponnusamy, S. et al., "In vivo model to determine fetal-cell enrichment efficiency of novel noninvasive prenatal diagnosis methods", *Prenat Diagn*, vol. 28, 2008, pp. 494-502.
Rainey, Paul B. et al., "Adaptive radiation in a heterogeneous environment", *Nature*, vol. 394, Jul. 2, 1998, pp. 69-72.
O'Brien, J. et al., "Investigation of the Alamar blue (Resazurin) fluorescent dye for the assessment of mammalian cell cytotoxicity", *AstraZeneca, Molecular Toxicology*, Alderley Park, Macclesfield, UK; Wilmington, DE 19840, USA.
Hojo, H. et al., "Differential IL-6 induction and liver injury in the rats given carbon tetrachloride through different routes", *Department of Hygienic Chemistry, Showa Pharmaceutical University*, Machida, Tokyo, Japan.
Wang, X.-J. et al., "The study on influence of ethanol ingestion on liver biotransformation enzymes and antioxidation", *Department of Internal Medicine*, Tianjin Tiantuo Hospital, Tianjin, China.
Ottesen, Elizabeth A. et al., "Microfluidic Digital PCR Enables Multigene Analysis of Individual Environmental Bacteria", *Science*, vol. 314, Dec. 2006, pp. 1464-1467, www.sciencemag.org.
Nunan, Naoise et al., "Spatial distribution of bacterial communities and their relationships with the micro-architecture of soil", *FEMS Microbiology Ecology*, vol. 44, 2003, pp. 203-215.
Nisisako, Takasi et al., "Formation of Droplets Using Branch Channels in a Microfluidic Circuit", *SICE*, Aug. 5-7, 2002, pp. 1262-1264.
Nisisako, Takasi et al., "Controlled formulation of monodisperse double emulsions in a multiple-phase microfluidic system", *Soft Matter*, vol. 1, 2005, pp. 23-27, www.rsc.org/softmatter.
Nisisako, Takasi et al., "Formation of Biphasic Janus Droplets in a Microfabricated Channel for the Synthesis of Shape-Controlled Polymer Microparticles", *Adv. Mater.*, vol. 19, 2007, pp. 1489-1493, www.advmat.de.
Nie, Zhihong et al., "Janus and Ternary Particles Generated by Microfluidic Synthesis: Design, Synthesis, and Self-Assembly", *J. Am. Chem. Soc.*, vol. 128, No. 29, 2006, pp. 9408-9412.
Marcy, Yann et al., "Nanoliter Reactors Improve Multiple Displacement Amplification of Genomes from Single Cells", *PLoS Genetics*, vol. 3, Sep. 2007, No. 9, e155, pp. 1702-1708, www.plosgenetics.org.
Nam, Jwa-Min et al., "Nanoparticle-Based Bio-Bar Codes for the Ultrasensitive Detection of Proteins", *Science*, New Series, vol. 301, No. 5641, Sep. 26, 2003, pp. 1884-1886, www.sciencemag.org.
Nam, Jwa-Min et al., "Bio-Bar-Code-Based DNA Detection with PCR-like Sensitivity", *J. Am. Chem. Soc.*, vol. 126, No. 19, 2004, pp. 5932-5933.
Ng, Joseph D. et al., "Protein crystallization by capillary counter-diffusion for applied crystallographic structure determination", *Journal of Structural Biology*, vol. 142, 2003, pp. 218-231.
Matsubara, Yasutaka et al., "Microchamber array based DNA quantification and specific sequence detection from a single copy via PCR in nanoliter volumes", *Biosensors and Bioelectronics*, vol. 20, 2005, pp. 1482-1490.
Lopez-Cortes, Alejandro et al., "Screening and Isolation of PHB-Producing Bacteria in a Polluted Marine Microbial Mat", *Microb Ecol*, vol. 56, 2008, pp. 112-120.
Liu, Jian et al., "A nanoliter rotary device for polymerase chain reaction", *Electrophoresis*, vol. 23, 2002, pp. 1531-1536.
Khademhosseini, Ali et al., "Microengineered hydrogels for tissue engineering", *Biomaterials*, vol. 28, 2007, pp. 5087-5092.
Knaak, James B. et al., "Development of partition coefficients, $V_{max}$ and $K_m$ values, and allometric relationships", *Toxicology Letters*, vol. 79, 1995, pp. 87-98.
Lapizco-Encinas, Blanca H. et al., "An insulator-based (electrodeless) dielectrophoretic concentrator for microbes in water", *Journal of Microbiological Methods*, vol. 62, 2005, pp. 317-326.
Laulia, Philips et al., "Stretched Cavity-Assisted Molding of Micrometer and Submicrometer Photopolymerized Hydrogel Particles", *Small*, vol. 4, No. 1, 2008, pp. 69-76, www.small-journal.com.
Jones, Keith et al., "Glowing jellyfish, luminescence and a molecule called coelenterazine", *Tibtech*, vol. 17, Dec. 1999, pp. 477-481.
Kaeberlein, T. et al., "Isolating "Uncultivable" Microorganisms in Pure Culture in a Simulated Natural Environment", *Science*, New Series, vol. 296, No. 5570, May 10, 2002, pp. 1127-1129.
Kaigala, Govind V. et al., "Automated screening using microfluidic chip-based PCR and product detection to assess risk of BK virus-associated nephropathy in renal transplant recipients", *Electrophoresis*, vol. 27, 2006, pp. 3753-3763, www.electrophoresis-journal.com.
Martin, Karin et al., "Generation of larger numbers of separated microbial populations by cultivation in segmented-flow microdevices", Lab Chip, 2003, pp. 202-207.
Gerritse, J. et al., "Complete degradation of tetrachloroethene by combining anaerobic dechlorinating and aerobic methanotrophic enrichment cultures" Appl Microbiol Biotechnol (1995) 43: pp. 920-928.
Gilbert, E.S., et al., "A constructed microbial consortium for biodegradation of the organophosphorus insecticide parathion", Appl Microbiol Biotechnol (2003) 61 pp. 77-81.
Kleinsteuber, Sabine et al., "Population Dynamics within a Microbial Consortium during Growth on Diesel Fuel in Saline Environments", Applied and Environmental Microbiology, May 2006, pp. 3531-3542.
Kohler, J. Michael et al., Chip Devices for miniaturized biotechnology, Appl Microbiol Biotechnol (2005) 69 pp. 113-125.
Munoz, R. et al., "Phenanthrene biodegradation by an algal-bacterial consortium in two-phase partitioning bioreactors", Appl Microbiol Biotechnol (2003) 61 pp. 261-267.
Wang, Zhi-Wu et al., "Potential of biofilm-based biofuel production", Appl. Microbiol Biotechnol (2009) 83 pp. 1-18.
Rosch, C. et al., "Approaches to assess the biodiversity of bacteria in natural habitats", Botanical Institute, The 11th Nitrogen Cycle Meeting 2005 pp. 169-173.
Buriti FC, et al., "Biopreservation by *Lactobacillus paracasei* in coculture with *Streptococcus thermophilus* in potentially probiotic and synbiotic fresh cream cheeses", J Food Prot. Jan. 2007;70(1) pp. 228-235.
Atencia, Javier, et al. "*Controlled Microfluidic Interfaces*", Nature, 2005, vol. 437, No. 29, pp. 648-655.
Gu,Hao, et al., "*Droplets Formation and Merging in Two-Phase Flow Microfluidics*", Int. J. Mol. Sci., 2011, vol. 12, pp. 2572-2597.
Shestopalov, Ilya, et al., "*Multi-Step Synthesis of Nanoparticles Performed on Millisecond Time Scale in a Microfluidic Droplet-Based System*", Lab-Chip, 2004, vol. 4, pp. 316-321.
Thorsen, Todd, et al., "*Dynamic Pattern Formation in a Vesicle-Generating Microfluidic Device*", Phys. Rev. Lett., 2001, vol. 86, No. 18, pp. 4163-4166.
Button, D.K., et al., "*Viability and Isolation of Marine Bacteria by Dilution Culture: Theory, Procedures, and Initial Results*", Applied and Environmental Microbiology, vol. 59, No. 3, Mar. 1993, pp. 881-891.
Connon, Stephanie A., et al., "*High-Throughput Methods for Culturing Microorganisms in Very-Low-Nutrient Media Yield Diverse New Marine Isolates*", Applied and Environmental Microbiology, vol. 68, No. 8, Aug. 2002, pp. 3878-3885.
Kingman, J.F.C., "*Stochastic Models for Random Sets of Points*", Poisson Processes, Oxford Studies in Probability-3, 1993, 5 pages.
Lederberg, Seymour, et al., "*Distribution and Activity of Single β-d-Galactosidase Centers Among Ribosomes of Escherichia Coli**", The Journal of Biological Chemistry, vol. 239, No. 1, Jan. 1964, pp. 54-58.
Schut, Frits, et al., "*Isolation of Typical Marine Bacteria by Dilution Culture: Growth, Maintenance, and Characteristics of Isolates Under Laboratory Conditions*", Applied and Environmental Microbiology, vol. 59, No. 7, Jul. 1993, pp. 2150-2160.
Beer et al., "*On-Chip, Real-Time, Single-Copy Polymerase Chain Reaction in Picoliter Droplets*", Anal. Chem., 2007, v. 79, pp. 847-8475.

(56) References Cited

OTHER PUBLICATIONS

Burns et al., "*Microfabricated structures for integrated DNA analysis*", Proc. Natl. Acad. Sci. USA, May 1996, vol. 93, pp. 5556-5561.
Pollack et al., "*Electrowetting-based actuation of droplets for integrated microfluidics*", Lab Chip, 2002, v. 2, pp. 96-101.
Vogelstein, et al., "*Digital PCR*", Proc. Natl. Acad. Sci. USA, Aug. 1999, vol. 96, pp. 9236-9241, Genetics.
Zheng et al., "*Formation of Droplets of Alternating Composition in Microfluidic Channels and Applications to Indexing of Concentrations in Droplet-Based Assays*", Anal. Chem., 2004, v. 76, pp. 4977-4982.
Kalinina, Olga, et al., "*Nanoliter Scale PCR with TaqMan Detection*," Nucleic Acids Research, vol. 25, No. 10, (1997), pp. 1999-2004.

* cited by examiner

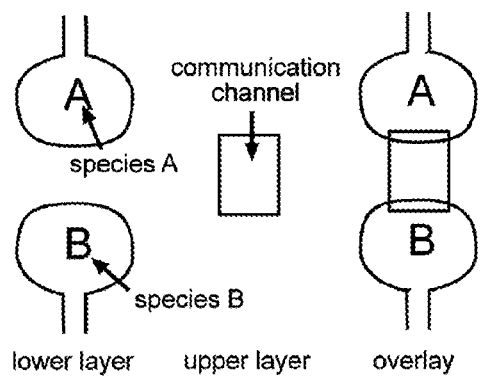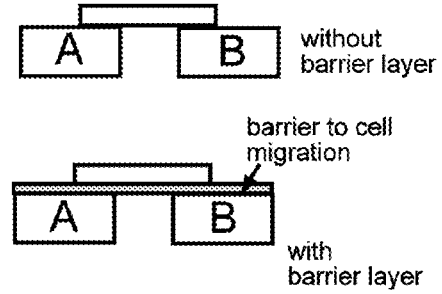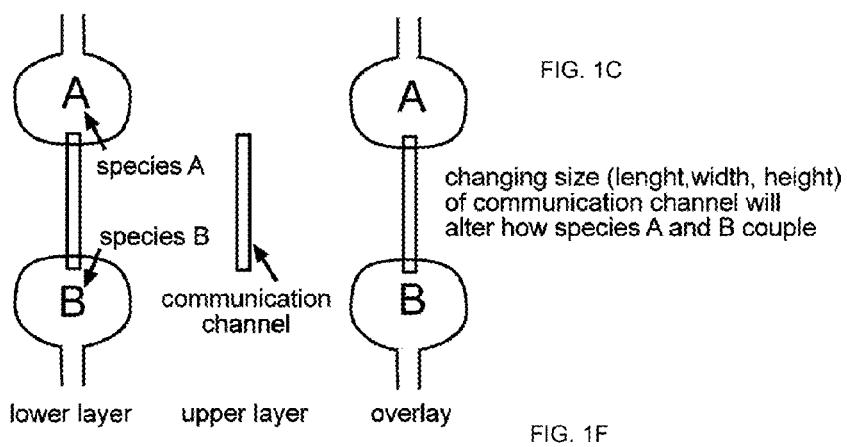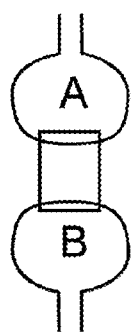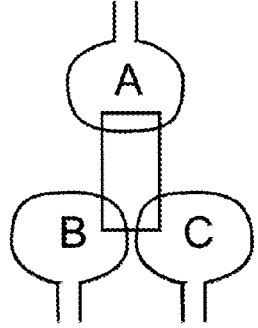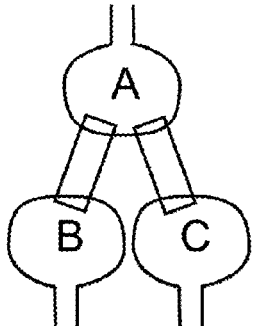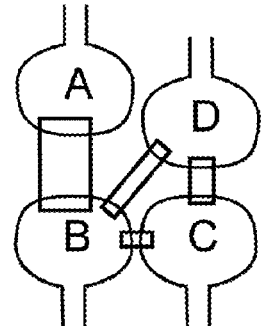

FIG. 2A
FIG. 2B
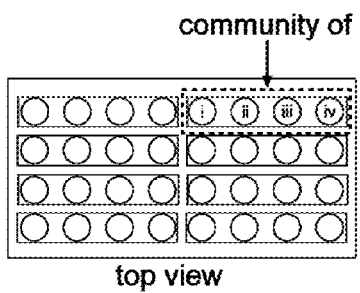
top view
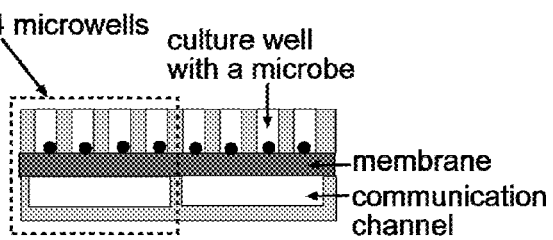
side view
FIG. 2C
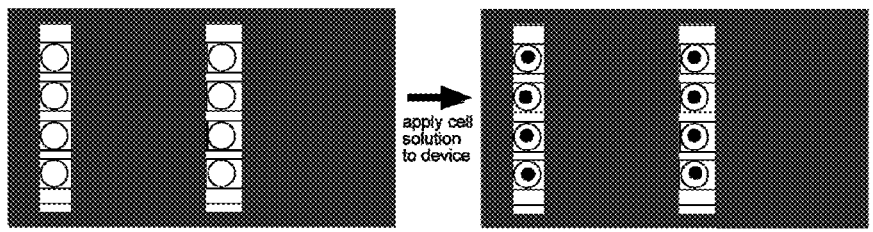
FIG. 2D
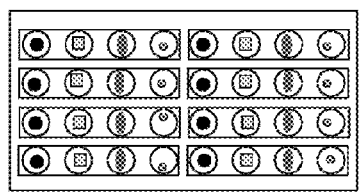
use stencil to create arrays of identical communities
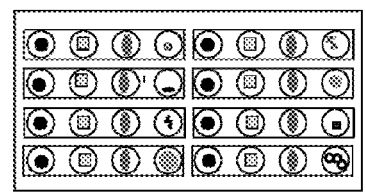
use stencil to create arrays of communities with one variable community member
FIG. 2E
FIG. 2F FIG. 3A
FIG. 3B
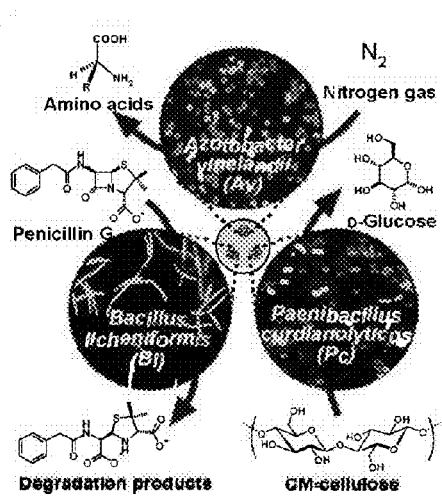
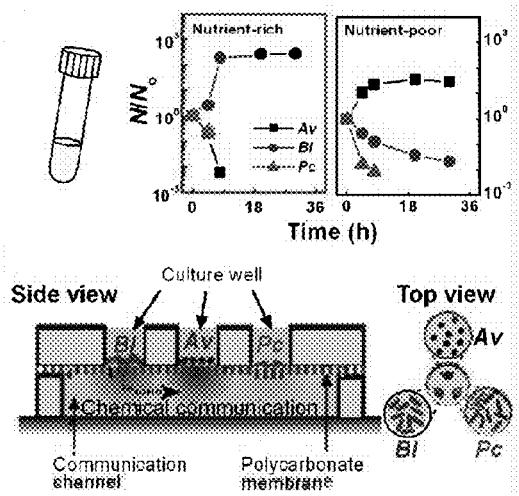
FIG. 3C FIG. 6A
FIG. 6B
FIG. 6C
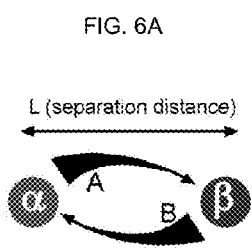
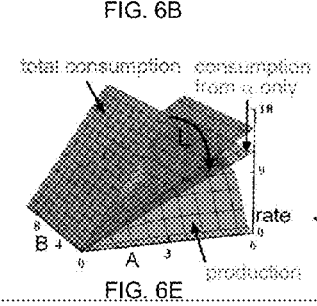
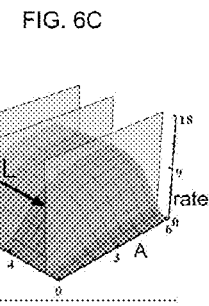
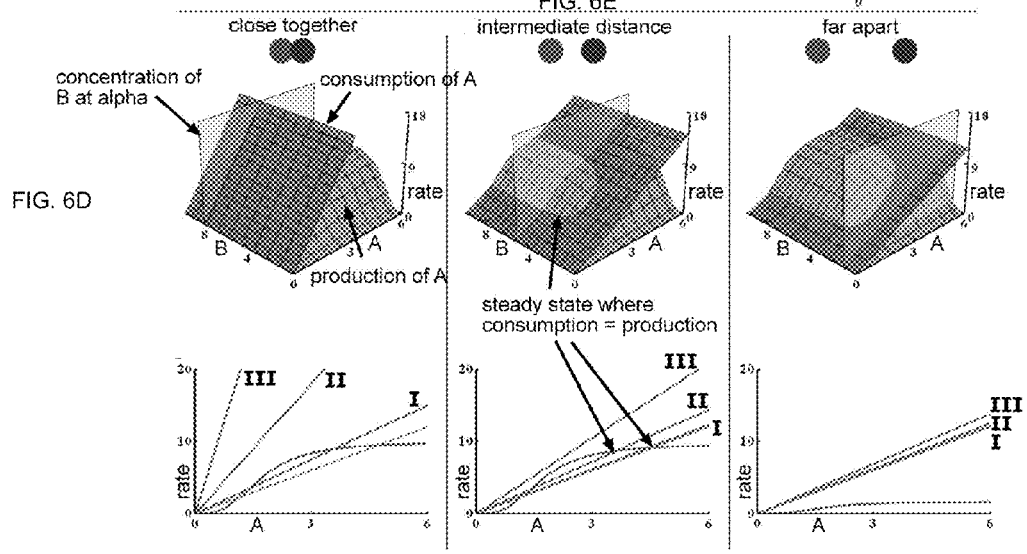
FIG. 6E
close together
intermediate distance
far apart
FIG. 6D
FIG. 6F
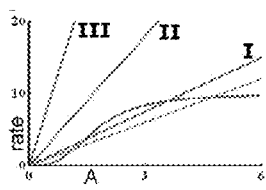
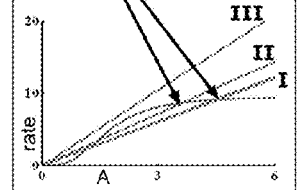
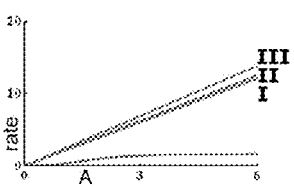
FIG. 6G
FIG. 6H
FIG. 6I FIG. 7A
Types of gel microdroplets
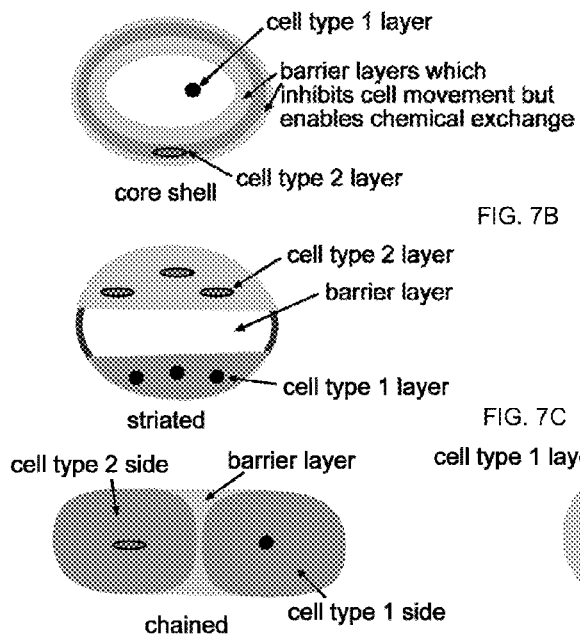
FIG. 7B
FIG. 7C
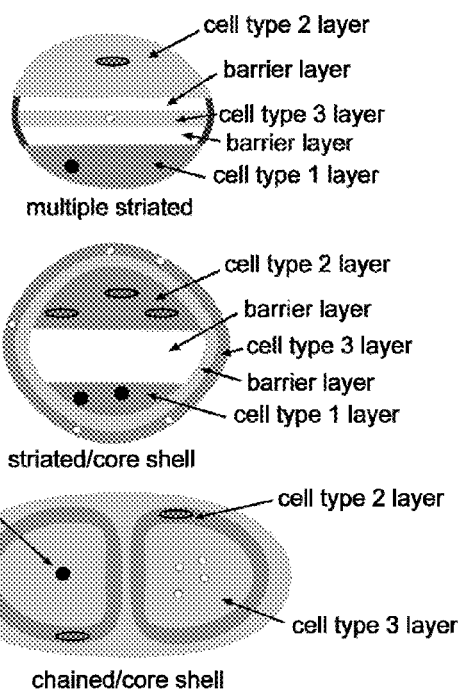

FIG. 8A         FIG. 8B         FIG. 8C
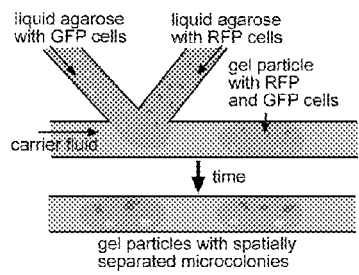
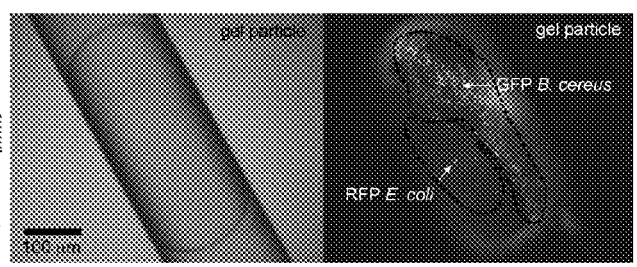

cross section of 1D device top view of 1D device cross section of 2D device top view of 2D device Example of resultant droplet

CO-INCUBATING CONFINED MICROBIAL COMMUNITIES

CROSS-REFERENCE TO RELATED APPLICATIONS

The present application is the national phase application of PCT Application No. PCT/US2008/071370, filed Jul. 28, 2008, which claims priority to U.S. Provisional Patent Application Ser. No. 60/962,426, filed Jul. 26, 2007, and U.S. Ser. No. 61/052,490, filed May 12, 2008, the entireties of all of which are herein incorporated by reference.

GOVERNMENT INTERESTS

This invention was made with United States government support under grant number 1 DP1 OD003584-01 awarded by the NIH Director's Pioneer Award program, part of the NIH Roadmap for Medical Research. The United States government has certain rights in this invention.

FIELD OF THE INVENTION

This invention is related to the field of methods and devices for co-incubating at least two different microorganisms, such that one of those microorganisms performs a function differently than it would if the second organism was absent.

BACKGROUND OF THE INVENTION

Microbial communities perform a wide range of functions, such as microbial growth, nitrogen processing in the soil, cellulose degradation, lignin degradation, dehalogenation of hydrocarbons and aromatic hydrocarbons, decomposition of organic matter in the carbon cycle, and environmental remediation such as oxidation of hydrocarbons. Many tasks are difficult or impossible for a single microorganism to perform. These functions typically require balancing competition and interactions among multiple species. For example, bacteria form biofilms and other forms of interactions, where several types of bacteria survive through symbiotic relationships, in which nutrients and signaling molecules are exchanged. These processes may be better performed by a synthetic community of microorganisms. Furthermore, some of these processes may require microorganisms that cannot be cultured without other microorganisms present.

The vast majority of bacteria cannot be cultured and cannot be studied with traditional techniques. Under homogeneous laboratory conditions, most attempts to co-incubate multiple microbial species do not result in stable communities due to lopsided competition for nutrients among the cultured species. Attempted methods of co-incubate have potential problems: different microorganisms may be toxic to one another on contact; they may need to be kept apart with in diffusion contact; one microorganism may grow at a much faster rate than others; shared molecules such as nutrients are lost by diffusion unless the microorganisms are cultured close together.

It is known that spatial structure influences competition and interactions between microbes. Environments in which the microbes live are highly spatially heterogeneous, and it has been shown that microbes exist as isolated patches. In nature, microbial communities inhabit matrices with intricate spatial structure, for example, many species of soil bacteria stably coexist as microcolonies separated by a few hundred micrometers. Thus, spatial structure is important in microbial ecology. However, spatial structure is difficult to control in natural environments and has not been systematically experimentally varied to understand its effect on the stability of bacterial communities.

It is also known that microbial communities perform important functions that require the stable interaction of multiple species. The combined effects of competition and chemical communication dictate that some multi-species communities have required spatial structures in order to stably function. The trade-off between reduced competition and effective communication define a specific range of spatial structures for each community. Spatial structures thus may be able to stabilize microbial communities. Natural habitats provide such spatial structures and recreating some communities in the laboratory will require culturing the microorganisms in specific structures and under specific conditions.

Aspects of methods for culturing communities of interacting bacteria, are disclosed in, for example: Swenson et al., 2000, *Environmental Microbiology* 2: 564-571 (artificial selection of microbial ecosystems for 3-chloroaniline biodegradation); in Swenson et al., 2000, *Proc. Natl. Acad. Sci. USA* 97: 9110-9114 (artificial ecosystem selection); and in Williams and Lenton, 2007, *Proc. Natl. Acad. Sci. USA* 104: 8918-8923 (artificial selection of simulated microbial ecosystems).

Aspects of how mixed communities do not survive due to competition are disclosed in, for example: Dechesne et al., 2008, *FEMS Microbiology Ecology* 64: 1-8 (limited diffusive fluxes of substrate facilitate coexistence of two competing bacterial strains); in Ferrari et al., 2005, *Applied and Environmental Microbiology* 71: 8714-8720 (microcolony cultivation on a soil substrate membrane system, which selects for previously uncultured soil bacteria); in Treves et al., 2002, *Microbial Ecology*, 45: 20-28 (two-species test of the hypothesis that spatial isolation influences microbial diversity in soil); in Hassell et al., 1994, *Nature* 370: 290-292 (species coexistence and self-organizing spatial dynamics); in Allison, 2005, *Ecology Letters* 8: 626-635 (cheaters, diffusion, and nutrients constrain decomposition by microbial enzymes in spatially structured environments); in Kerr et al., 2002, *Nature* 418: 171-174 (local dispersal promotes biodiversity in a real-life game of rock-paper-scissors); and in Rainey and Travisano, 1998, *Nature* 394: 69-72 (adaptive radiation in a heterogeneous environment).

Aspects of how dependent microbial strains require close proximity are disclosed in, for example: Nunan et al., 2003, *FEMS Microbiology Ecology* 44: 203-215 (spatial distribution of bacterial communities and their relationship with the micro-architecture of soil); in Hansen et al., 2006, *Nature* 445: 533-536 (evolution of species interactions in a biofilm community); and in Nielsen et al., 2000, *Environmental Microbiology* 2: 59-68 (role of commensal relationships on the spatial structure of a surface-attached microbial consortium).

Aspects of how function and viability of some strains requires partner strains are disclosed in, for example, Ohno et al., 1999, *Biosci. Biotechnol. Biochem.* 63: 1083-1090 (establishing the independent culture of a strictly symbiotic Bacterium *Symbiobacterium thermophilum* from its supporting *Bacillus* strain); in Kaeberlein et al., 2002, *Science,* 296: 1127-1129 (isolating "uncultivable" microorganisms in pure culture in a simulated natural environment); in Ou and Thomas, 1994, *Soil Science Soc. Am. J.* 58: 1148-1153 (influence of soil organic matter and soil surface on a bacterial consortium that mineralizes fenamiphos, a pesticide); in Kato et al., 2005, *Applied and Environmental Microbiology* 71: 7099-7106 (stable coexistence of five bacterial strains as a cellulose-degrading community); in Price-Whelan et al., 2006,

*Nature Chemical Biology* 2: 71-78 (rethinking 'secondary' metabolism: physiological roles for phenazine antibiotics); and in Cosgrove et al., 2007, *Applied and Environmental Microbiology* 73: 5817-5824 (different fungal communities are associated with degradation of polyester polyurethane in soil).

Aspects of how soil is spatially complex, with patchy distribution of microbes, are disclosed in, for example, Young and Crawford, 2004, *Science* 304: 1634-1637 (interactions and self-organization in the soil-microbe complex); and in Grundmann et al., 2001, *Soil Science Soc. Am. J.* 65: 1709-1716 (spatial modeling of nitrifier microhabitats in soil).

Aspects of methods for in vitro spatial culture are disclosed in, for example, Abhyankar and Beebe, 2007, *Anal. Chem.* 79: 4066-4073 (spatiotemporal micropatterning of cells on arbitrary substrates); in Weibel et al., 2007, *Nature Reviews Microbiology* 5: 209-218 (microfabrication meets microbiology); in Keymer et al. 2006, *Proc. Natl. Acad. Sci. USA* 103: 17290-17295 (bacterial metapopulations in nanofabricated landscapes); and in Ingham et al., 2007, *Proc. Natl. Acad. Sci. USA* 104: 18217-18222 (the micro-Petri dish, a million-well growth chip for the culture and high-throughput screening of microorganisms).

BRIEF SUMMARY

The present invention provides a device for co-incubating microorganisms, comprising a lower layer, and upper layer and a barrier. The lower layer comprises a first compartment for a first microorganism and a second compartment for a second microorganism (different than the first). The first and second compartments are physically separated by a distance x. The upper layer comprises at least one communication channel. The lower layer and the upper layer are positioned such that the communication channel overlays the first and the second compartments. The barrier isolates the microorganisms in one compartment from those in another compartment, but allows culture products to pass between compartments via the communication channel in the upper layer.

The present invention also provides a device for co-incubating microorganisms, comprising a gel microdroplet. The gel microdroplet comprises at least two areas: a first area with a first microorganism and a second area with a second microorganism (different than the first). The first and second areas are physically separated by a distance x. The microorganisms are in a gel that prevents their migration from one area to another. Alternatively, the two areas can be separated by a layer that prevents their commingling.

One important feature of the devices of the present invention is that they provide for compartmentalized culturing of microorganisms. A compartment may refer to separate division or section and can take a variety of forms, geometries, and shapes, e.g. it can be a well, chamber, channel, droplet, bead, plug, etc. In general, what is important is that the compartment provides for a confined area where a particular type of microorganism may be cultured without being intermixed with a different type of microorganism. Thus, a multitude (two or more) compartments provide culturing space of two or more different species of microorganisms without any cross-contaminations. Localized growth of a single microbial type (e.g. strain, species) in a single compartment is important for the confined culturing method of these devices. From a single microbe these devices enable one to grow the microorganisms in a tiny separated culture compartment. Based on this concept, it may be possible to culture pre-mixed bacterial broth with several different species. By dilution and stochastic seeding into the culture compartments of a device, it is possible to culture a single species in a single culture well as long as the culture broth is diluted enough to adjust the appropriate cell density as the number of culture compartments in a device.

The devices of the present invention can be used in a method for co-incubating at least two different microorganisms such that at least one of the microorganisms performs a function differently than it would if the second organism was absent. This method can be used in various applications described below.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 1 is a schematic drawing of a device for co-incubating microorganisms according to the present invention, which illustrates how individual microorganism (or microorganism culture) wells can be connected with various 3D spatial architectures.

FIG. 2 is a schematic drawing that illustrates the concept of using stencils to control the loading of cells into compartments on a microfluidic device.

FIG. 3 shows schematic drawing (a, c) and a graph (b) that illustrate the concept of how a synthetic community of three microorganism species requires spatial structure to maintain stable coexistence.

FIG. 6 (*a-i*) shows a schematic drawing and graphs illustrating a mathematical model of a two-species syntrophic microbial community.

FIG. 7 is a schematic drawing that illustrates some possible embodiments of co-incubating of microorganisms using gel microdroplets (GMDs).

FIG. 8 shows one schematic drawing and two microscopic images of the plug-based microfluidic techniques can be used to generate gel microdroplets for spatially structured co-incubates of microbial cells.

DETAILED DESCRIPTION OF THE PRESENTLY PREFERRED EMBODIMENTS

Figures 4A, 4B, 4C:
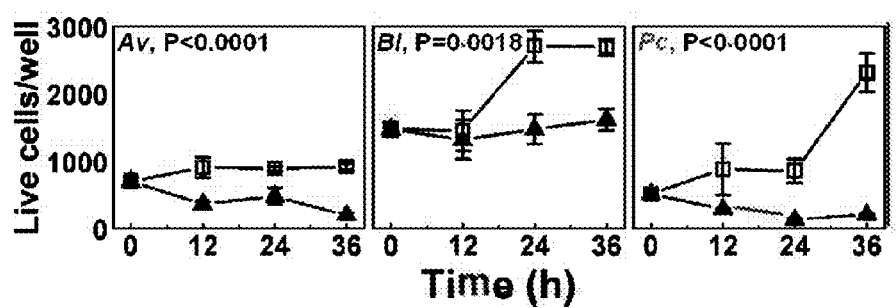
FIG. 4 shows graphs that illustrate how the stability of the community requires communication among the microbial species (three in the example shown).

For the purpose of promoting an understanding of the principles of the invention, reference will now be made to certain preferred embodiments thereof and specific language will be used to describe the same. It will nevertheless be understood that no limitation of the scope of the invention is thereby intended. Any alterations, further modifications and applications of the principles of the invention as described herein are being contemplated as would normally occur to one skilled in the art to which the invention relates.

Certain features disclosed in the below-referenced patents, patent applications, and other references are related to the present invention and their disclosures are herein incorporated by reference.

Definitions

In biological terms, a "community" is a group of interacting organisms sharing an environment. A "microbial community" is a community of microorganisms, i.e. microbes. The term "microorganism" refers to both refers to both prokaryotic and eukaryotic microorganisms, including, for example bacteria, protozoa, viruses, or fungi. In microbial communities, resources, preferences, and a number of other conditions may be present and common, affecting the identity of the community members and their degree of cohesiveness. As one example of a microbial community, a gut bacterial community refers to the collection of discrete bacterial species that are present in the gut, and that may contribute to each others' survival by providing nutrients or processing wastes. It is contemplated that the term "microbial community" refers to two or more different microbes, or populations of microbes. A microbial community (or simply "community") could thus include two or more microorganisms, two or more strains, two or more species, two or more genera, two or more families, or any mixtures of the above. The interaction between the two or more community members may take different forms. For example, interactions among various community members may be competitive, they may be mutually beneficial, or they may be mutually harmful (e.g., via production of toxic products, competition for nutrients, etc), as long as the interactions together can provide a function or a structure that is not available through either one individual community member. The devices and methods of the present invention might provide one or more community members with conditions that allow those members to perform certain function while reducing accompanying undesirable or harmful effects. In one embodiment, the present invention provides for conditions that enable culturing of microorganisms that in nature prefer mutually less compatible, incompatible, or exclusive conditions, such as different partial concentration of oxygen, different pH, different composition of nutrients, etc. The cultivation of some microbial communities may require externally controlled environments that can be provided according to the present invention. Some microbial communities may distinguish themselves by producing, consuming, modifying, degrading, and/or accumulating particular compounds. There are also microbial communities that can over time themselves create preferred different environments (e.g. aerobic, anaerobic, facultative anaerobic, etc.), again by producing, consuming, modifying, degrading, and/or accumulating particular compounds. The practice of the present invention specifically contemplates all of the above types of microbial communities.

In biological terms, "culture" is the act or process of cultivating living material (as microbes, e.g. bacteria or viruses) in prepared nutrient media; culture also refers to a product of such cultivation. Culturing of microorganisms may be performed by inoculating a known concentration of microorganisms into a solution (culture medium typically containing nutrient media; optionally nutrient media that is modified, that contains desired additives, etc.) and measuring growth over time. Growth of cultured microorganisms can be measured in a variety of ways, including direct counts of microorganisms, plate counts of colony forming units, and turbidimetric measurements.

"Culture medium" (also called "nutrient medium", "growth medium", and "medium") refers to a substance, either solid or liquid, used for the incubation, cultivation, isolation, identification, or storage of microorganisms. Culture medium may include various components such as nutrients and optionally a variety of additives, including minerals, vitamins, amino acids, peptides, hormones, cell culture extracts of unknown composition, cell lysates of unknown composition, etc. The composition of the culture medium may differ when different types of microorganisms are cultured. The culture medium may optionally be modified (e.g. some compounds may be omitted from the culture medium when one wants to starve the microorganisms, or one wants to apply selection pressure).

"Co-incubation" of microorganisms refers to joint incubation or incubation together, of two or more types (e.g. organisms, populations, strains, species, genera, families, etc.) of microorganisms. In the context of the present invention, co-incubation of microorganisms refers to the joint incubation of two or more types of microorganisms in a microbial community. Co-incubation of microorganisms is also meant to include co-culture (i.e., joint culture, or culture together) of microorganisms, but growth is not required for co-incubation.

"Syntrophy" refers to a biological relationship in which microorganisms of two or more different species or strains are mutually dependent on one another for nutritional requirements. A set of such microorganisms are "syntrophic." Communities may perform "syntrophic functions" if the function is dependent on the exchange of chemicals/enzymes/molecules/proteins/genetic material. A "syntrophic function" requires at least two community members to be present and the role of at least one community member is dependent on a chemical received from at least one other community member. While in some embodiments of co-incubation the co-incubated microorganisms can be syntrophs, not all embodiments of the present invention require this feature. Community function thus refers to a syntrophic function, or any other function that is enhanced by the co-incubation of more than one organism in the community, and includes functions such as such as growth of microorganisms, degradation or removal of external components, production of incubation components, etc.

An "antimicrobial" is a substance (e.g., drug) that kills or inhibits the growth of microbes (microorganisms) such as bacteria, fungi, or viruses. Antimicrobials either kill microbes (microbicidal) or prevent the growth of microbes (microbistatic). Antimicrobials include antibiotics, antivirals, antifungals, antiparasitics, and synthetically formed compounds as well. The antimicrobials used in the practice of the present invention also may be non-pharmaceutical, for example they may include essential oils having antimicrobial activity, heavy metal cations (e.g., colloidal silver, $Hg^{2+}$, $Cu^{2+}$, $Pb^{2+}$) having antimicrobial activity, etc.

Microfabricated Devices

The present invention provides a device for culturing microorganisms, comprising (a) a lower layer comprising a first compartment and a second compartment, physically separated from the first compartment by a distance x, (b) an upper layer comprising a communication channel; and (c) a barrier positioned between the lower layer and upper layer, wherein the barrier is impermeable to the microorganisms and permeable to soluble compounds; wherein the lower layer and the upper layer are positioned such that the communication channel overlays the first and the second compartments.

In one embodiment, the device of the invention may have dimensions between about 0.3 cm to about 15 cm per side and thickness of about 1 μm to about 1 cm, but the dimensions may also lie outside these ranges. The surface of the upper and lower layers can be smooth or patterned. When multiple layers are present, different layers can have different surfaces.

The upper and lower layers can be formed from a suitable material such as a polymer, metal, glass, composite, or other relatively inert materials.

The compartments of the upper layer are sized and shaped to be suitable for culturing a microorganism. The upper layer comprises at least two compartments (See FIG. 1, compartments A and B). Any number of compartments can be present (See FIG. 1, compartments A-D).

The compartments are separated by a distance x. In general, the distance can be anything that allows physical separation of the microorganisms. Typically, it is between about 50 µm and about 500 µm, preferably between 100 µm and about 300 µm.

The compartments may be connected to culture media channels to allow addition, removal or continuously replacement of culture media in the compartments.

In some examples (e.g. for high throughput experimentation), multiple upper layers (i.e., those containing compartments) can be present. In this embodiment, one upper layer may contain a set of compartments with one set of microorganisms, and another upper layer may contain another set of microorganisms. A lower layer could then be positioned between with two upper layers with a barrier layer separating each upper layer from the lower layer (the barrier layers could be the same or different). More than two layers may be used in the fabrication of the device as well.

The communication channel is sized and shaped such that when the upper layer is positioned over the lower layer, the channel overlays (or links) at least two compartments. Multiple communication channels can be present. In some cases all the communication channels will overlay the same compartments (parallel). In some cases, the entire lower layer can be the communication channel.

Typically, the communication channel is larger than the distance x between the two compartments, so as to overlap into each compartment. Typically it is between about 50 µm and about 500 µm, preferably between 100 µm and about 300 µm.

The compartments may be connected non-directionally (e.g., by diffusion through the communication channel) or directionally (e.g., using flow through the communication channel). Alternatively, compartments may be connected to combinations of other compartments using both non-directional and directional communication channels. Some compartments may not have influx of nutrients (e.g. by controlling flow away from those compartments or by using barriers impermeable to those nutrients).

When multiple compartments are present in the upper layer, the communication channel(s) can overlay all of the compartments or just select compartments. In the latter case, further channels can be present to link further compartments (See FIG. 1, compartments A and B, B and C, B and D, and C and D linked via channels).

The barrier is a structure that blocks passage of microorganisms from one compartment to another, but allows soluble compounds to pass from one compartment to another. The barrier according to the present invention can be a membrane, gel, nanostructure, pore, or any other structure that is not permeable to microorganisms but permeable to components of interest, such as molecules, complexes, assemblies, etc. Examples of membranes useful in the culture of bacteria are shown in Kaeberlein et al., 2002, *Science*, 296: 1127-1129, incorporated herein by reference. In certain embodiments of the invention, the barrier itself may include one or more desired molecules, one or more cells, or one or more microorganisms; for example, the barrier may include a biofilm.

The dimensions, geometry, and size of the barriers may vary and will depend on the microorganisms that need to be confined and/or separated. For example, if the goal is to co-incubate bacteria, the general size of bacteria is about 2-3 µm. The sizes of the barriers that separate the bacterial compartments should be approximately below about 0.1 µm. The typical cut-off size of membrane for the filtration of bacterial culture broth is about 0.45 µm, but in some cases smaller size of bacteria can be shown. In terms of bacterial moving, migrations speed of bacteria has been known as 5-10 µm/s. In general, the devices of the present invention should be able to deliver fresh media or stimuli to the microbes, while allowing communication among colonies.

In an alternate embodiment, barriers are not present and the microorganisms are instead tethered/trapped in the compartments (for example, in gel particles, posts or other traps).

The compartments and communication channels can have different dimensions and geometries such as length, width, thickness, depth, and can also have different form of cross-sections, including square, rectangle, triangle, circular cross-section, etc. The compartments, channels, etc. can also have different dimensions and geometries (FIGS. 1-4).

In one example of a device of the present invention, the upper layer comprises 100 nm culture wells separated from each by approximately 500 µm. In the lower layer, a communication channel overlays the wells in the upper layer. A polycarbonate membrane separates the upper and lower wells. Above the culture wells, each culture well may be connected with individual media channels of 5 µm hole (Ismagilov et al., 2001, *J. Anal. Chem.* 73: 5207-5213).

Droplets

The present invention also provides droplets for co-incubating microorganisms. The droplets comprise at least two areas: a first area with a first microorganism and a second area with a second microorganism (different than the first). The first and second areas are physically separated by a distance x. The droplets are composed of a material that prevents migration of microorganisms from one area to another. Alternatively, the two areas can be separated by a layer that prevents their commingling.

In general, a "droplet" refers to a relatively small volume of material. Droplets according to this invention can be polymeric or solid particles, gel microdroplets, beads, or plugs.

Suitable droplets may have different shapes and sizes. The droplets may have different sizes and geometries, and may be symmetric or asymmetric. For example, droplets may refer to a single sphere or oval, may refer to a core-shell configuration, to a group of smaller particles attached together (e.g. to form grape-like structure), to a string of particles some of which are in contact with each other, etc. In general, the droplets have a volume of between about $1 \times 10^{-9}$ microliters to about $1 \times 10^3$ microliters. If spherical or roughly spherical, the droplets typically have a diameter between about 1 µm to about 1.00 mm, and preferably between about 1 µm and about 500 µm.

Droplets may contain two or more, if desired multiple, types of microorganisms or colonies of microorganisms. Each type of microorganisms may be positioned anywhere in or on the droplets (so long as at least one type is confined from at least one other type). Alternatively, microorganisms may be encapsulated in the droplets.

Gel Microdroplets

A "gel microdroplet" (GMD) (also referred to herein as a gel bead, or a gel particle) refers to very small droplets, i.e. very small volume entities comprised of gel (and optionally liquid) material, and which can contain zero, one or multiple biological entities. For example, two or more types of bacteria may be encapsulated in agarose GMDs. In particular, aqueous droplets containing bacteria, growth media, and liquid agarose may be formed in fluorinated oil. The GMDs may optionally contain inorganic and/or organic chemical compounds;

these compounds may optionally be in solution. GMDs have volumes which may be defined by a boundary comprised of another liquid, such as a non-aqueous fluid, or by a permeability barrier such as a membrane, such that the membrane is capable of retaining biological entities (e.g. microbes) of interest within a GMD, and also capable of passing other biological entities such as molecules (smaller than microbes). For example, it would be possible to generate two or more streams of two or more different microorganism strains, then combine them into a single droplet, and then polymerize it into a GMD (e.g. agarose GMD), where the microorganism strains are compartmentalized and spatially separated, i.e. they are not in direct contact with each other. Although GMDs can be of any shape, GMDs are often approximately spherical because of the tendency of forces associated with the boundaries of GMDs to round up the deformable GMDs. Other forces, for example hydro-dynamic shear associated with stirring a GMD suspension, adhesion to a surface, or gravity, tend to cause departure from a spherical shape. Further, GMDs which contain or occupied by entities whose volume is a relatively large fraction of the GMD volume can result in GMDs which are non-spherical. Thus, for example, cell or a population of cells surrounded by a thin gel coating (and optionally with an aqueous solution), which in turn is surrounded by a non-aqueous fluid, is a GMD. Similarly, a non-biological particle s surrounded by a thin gel coating (and optionally with an aqueous solution), which in turn is surrounded by a non-aqueous fluid, is also a GMD.

When spherical, GMDs have diameters between about 1 μm to about 30 mm, and preferably between about 5 μm and about 1000 μm. Generally, GMD volumes are between about $1 \times 10^{-12}$ to about 10 ml, preferably between about $1 \times 10^{-10}$ to about 1 ml. FIG. 7 schematically illustrates some possible embodiments of co-incubating of microorganisms using GMDs. Examples of various encapsulating approaches are shown. The inventors have been able to grow microbial cultures in certain types of GMDs.

Various types of gels can be used in the practice of the invention. They include: standard gel, when growth and potential of mixing of bacteria is slow or is not a concern; gels that are impermeable to microorganisms, so the microorganisms do not move through the gel; and arbitrary gels, where the interfaces among the gels have membranes impermeable to microorganisms, yet permeable to desired chemicals. When generating gel beads, such membranes could be formed chemically as the beads are being made, e.g. by reacting two polymers on the surface of the bead, or by incorporating those two polymers into the individual gels, so at interfaces of gels membranes form. The formation of gel or polymeric substances in a plugs could also be initiated by an externally by light, temperature change, additional of a small molecule, pH change, pressure change, contact with carrier fluid, or contact with channel walls.

It is possible to insert a relatively hydrophobic intermediate layer between the layers including different species 1 and 2. For example, a single GMD can comprise the one half spheres of species 1 and the other half sphere of species 2, and between the half spheres a disk-like layer is inserted. This disk-like layer provides relatively hydrophobic environments, which enhance the mass transport of hydrophobic compounds (products, intermediates, etc.). Biosynthesis via co-incubation of species 1 and 2 can be promoted by the intermediate layer that induces close contact of hydrophobic compounds near the each layer.

In another embodiment, a two-layer GMD microfluidic device, which is separated by the relatively hydrophobic intermediate layer, can be used. On both sides of layers, different species of 1 and 2 are inoculated for the co-incubation, then the hydrophobic precursor A by species 1 can easily migrate to intermediate layer, then the species 2 tightly connected into the intermediate layer convert the precursor A into the final product X.

As well, it is possible to use a double-layered GMD, which is constructed by the core sphere of species 1, and the species 2 covers the core like shell. Between the core and shell of GMD, relatively hydrophobic intermediate layer is inserted. Examples of relatively hydrophobic intermediate layers can be found in Fernandez-Lafuente et al., 1998, Chemistry and Physics of Lipids 93: 185-197.

The processes for making gel microdroplets may involve forming first GMDs, and subsequently processes for forming GMDs where the first GMDs are incorporated within second GMDs. This yields GMDs with two or more distinguishable regions, and can be extended to the formation of composite GMDs with a plurality of distinguishable gel regions. The various gel regions can be provided with different properties, or used to entrap biological entities at different relative locations within GMDs, or used to provide or entrap assay-assisting entities at different locations within GMDs. Further, one or more gel regions can be subsequently liquefied, such that composite GMDs with one or more interior liquid regions are formed. Composite GMDs may also be formed where two or more types (e.g. species) of microorganisms are mixed together. Thus, in some embodiments of the present invention, gel droplets or other types of particles that would structure the position of microbial cells (by imposing boundaries on the movement of cells within in the particle, either by immobilizing them in a gel or having a particle with liquid compartments separated by a barrier) can be used to create co-incubated cultures of cells with spatial structure. Several methods have been established for the creation of such particles, including using microfluidic techniques to generate Janus (two-sided) particles and either using a gelation mechanism or polymerization process to make the structure of the particle permanent. Such particles could also be made using micromolding techniques or self-assembly techniques. Important parameters in the design of a particle for co-incubation include: 1) distance between the different types of cells; 2) total size of the particle; 3) the volume of the particle available to each type of cell; 4) length of the diffusion path connecting the different cell types to each other and also to the external environment (tortuosity of the path and iterations of various molecules with the particle material); 5) ratio of the number of different types of compartments; 6) the topology of network of compartments inside particles (side by side, inside vs. outside, 3 compartments connected in a line vs. in a triangle, which compartments have access to external environment); 7) compartments in which some types of cells are excluded but not others (partial mixing of some compartments).

In some embodiments, this invention contemplates the use of GMD particle technology to generate co-incubated cultures that can be used in a fermentation tank, or spread around the environment to degrade unwanted stuff or accumulate desirable stuff (gold, plutonium, etc.) One way to practice this invention is to create GMDs (layer by layer, or composites) that get better results than simply mixing microorganisms in a flask (for example, locally high concentration of metabolites, local consumption of waste, or a combination of high oxygen outside and low oxygen inside the particles—something that would typically be hard to do in a single fermentation tank). In addition, it is possible to control whether microorganisms mix or don't mix before microdroplets polymerize.

The present invention contemplates encapsulation of microbial cells. Encapsulation may be used for making GMD-like particles and enclosures. Aspects useful for encapsulating confined and separated microbial communities may be found in, for example: United States Patent Application Pub. No. 20060051329 (microfluidic device for the encapsulation of cells with low and high cell densities); in Green et al., 2008, *Advanced Functional Materials* 15: 917-923 (biomineralized polysaccharide capsules for encapsulation, organization, and delivery of human cell types and growth factors), all of which are incorporated herein by reference. Thus, in one aspect, this invention provides for the generation of bead-in-bead capsules consisting of spatially separated cell populations and with temporally separated biomolecule release.

Beads

In another embodiment, the droplets contains two or more beads. Each bead can be of the same or different type, shape, and size. Beads may be connected. The beads may be gel beads, for example they may be agarose beads. By putting individual strains or species of microorganisms onto beads (where each bead has only one strain or species), and then mixing beads in the right ratios, a community can be created that includes a variety of members, e.g. members who are toxic to one another on contact. Compound beads may be generated as well, with one type of microorganism in each half (or part) of the bead. Layered beads may be generated, where each layer will have discrete types of microorganisms.

The beads may be in homogeneous or heterogeneous layers of the microdroplet, e.g. the microdroplet may be core-shell, side-by-side, etc.

Intermediate layers may be used to create additional spacing (distance) between the microorganisms. Such intermediate layers may or may not have microorganisms. One layer containing one type of microbes may be surrounded (coated) by another layer containing another type of microbes, etc. Multiple layers may be used, to produce multilayered beads with a plurality of microbes. The bead assembly could rely on surface tension or the Torii or Weitz methods for making double emulsions (Nisisako et al., 2005, *Soft Matter* 1: 23-27; Utada et al., 2005, *Science* 308: 537-541.

FIGS. 7-10 illustrate schematics of various examples of droplets useful for practicing the present invention.

In some examples, by making beads magnetic, the beads can be distributed in the desired area, e.g. environment, and then easily picked up when desired, for example, by using an electromagnet or a permanent magnet, when the beads are no longer needed.

Plugs

Droplets can be liquid (usually aqueous) which exists either in a two-phase system (e.g., organic phase/aqueous phase, fluorous phase/aqueous phase) or in a single phase with an emulsifying agent/surfactant (e.g., aqueous droplets surrounded by aqueous bulk solution). A "plug" is a specific type of droplet (Song et al., 2006, *Angew. Chem. Int. Ed.* 45: 7336-7356; Chen et al., 2006, *Curr. Opin. Chem. Bio.* 10: 226-231).

Formation of liquid plugs was previously described by this inventor in U.S. Pat. No. 7,129,091. In the present invention, different types of microorganisms are introduced into different plug fluids.

Methods of incorporating multiple and different microbes into a spatially structured plug include combination of fluids containing microbes with fluids containing components necessary to form a gel or a polymer or a solid matrix. Upon forming the plug, the different types of microbes would have a non-uniform spatial distribution throughout the plug and this initial spatial distribution can be controlled using microfluidic techniques such as laminar flow of multiple streams. Before the microbes are able to substantially intermix, the components would form a gel or a polymer or a solid matrix and prevent significant further intermixing of the microbes. In this way, the non-uniform distribution of the microbes in the plug would be preserved. Formation of a gel or a polymer or a solid matrix could be accomplished in a number of ways, including spontaneous formation, as takes place when a supercooled gel or solid transitions from a liquid state into a gel or solid state; stimulation formation, as takes place when pressure, temperature or UV or visible light or another form of radiation is applied, or a chemical reagent is added. Chemical reagents include cross-linking agents, changes in pH, change in ionic composition, or the additional of a small molecule, ions, or a macromolecule. Chemical reagents may be pre-loaded into the plug fluids, or added after the formation of a plug.

In addition, methods of incorporating multiple and different microbes into a spatially structured plug include sequentially forming layers containing microbes. In this method, a plug containing microbe A would be coated with a barrier layer consisting of either a gel or a polymer or a solid matrix that would inhibit the movement of microbes across the barrier. A layer of microbe B could then be formed outside of the barrier layer. In this way, microbes A and B would exist in the same plug separated by a barrier which prevents microbes A and B from mixing. Controlling the type of barrier layer, the thickness of the barrier layer, and the number of barrier layers in the plug could be used to control the spatial structure of the plug containing multiple types of microbes. The barrier layer may not be always necessary in these applications. If the gel or a polymer or a solid matrix in which either microorganism A or B are embedded do not allow migration of the organism, the barrier layer is not required.

In addition, methods of incorporating multiple and different microbes into a spatially structured plug include combinations of plugs into larger objects. A plug is made containing microbe A. A separate plug is made containing microbe B. The plugs form a gel of polymeric matrix using methods described above. The plugs are then physically combined such that there is a chemical exchange path connecting the microbes A and B. Additionally, separator plugs could be used to control the amount of space between the plug containing microbe A and the plug containing microbe B.

Another method of using plugs to co-incubate multiple microbes in a structured space would be to allow the carrier fluid of the plug to transport chemicals between adjacent plugs. In this way, plugs containing different microbes could be positioned in a microfluidic device and adjacent plugs could exchange chemical information.

Forming particles containing multiple interacting microorganisms is not limited to the use of plugs. Beads or gel or solid or polymer particles containing microorganisms may be directly combined into larger objects containing multiple interacting microorganisms. A barrier layer impermeable to microorganisms but permeable to exchanging molecules may be used to bind particles containing different microorganisms together. Alternatively, such particles may be held together by an external membrane impermeable to microorganisms but permeable to exchanging molecules.

Forming particles containing multiple interacting microorganisms may be accomplished by generating a long string of gel or a polymer or a solid matrix containing the first microorganism, generating a long string of a gel or a polymer or a solid matrix containing the second microorganism, then connecting the two strings lengthwise, and then cutting the combined strings perpendicular to the direction of the strings to produce particles containing both organisms. Strings may be obtained by extrusion or any other method commonly used for forming polymeric fibers. This method is not limited to two strings; three or more strings may be used in this way to produce particles containing three or more different microorganisms.

Forming particles containing multiple interacting microorganisms may be accomplished by generating a sheet of gel or a polymer or a solid matrix containing the first microorganism, generating a sheet of a gel or a polymer or a solid matrix containing the second microorganism, then connecting the two sheets face to face, and then cutting the combined sheets perpendicular to their long dimensions to produce particles containing both organisms. Sheets may be obtained by extrusion, molding, or any other method commonly used for forming polymeric sheets and films. This method is not limited to two sheets; three or more sheets may be used in this way to produce particles containing three or more different microorganisms.

Forming particles containing multiple interacting microorganisms may be accomplished by direct molding, such as provided by Pattern Replication In Non-wetting Templates technologies such as that provided by Liquidia technologies (described, for example, in US 2007/0178133 A1 and http://www.liquidia.com/technology_platform.html which are incorporated here by reference)

The methods described above can be used to construct communities of two or more different microbes. The spatial structure of the community can be controlled including: separation distance between the microbes, ratio of microbes inoculated, pattern of connectivity (for example three types of microbes with all three possible connections, versus three types of microbes connected with only two connections), total volume of the space, and tortuosity of chemical exchange path between microbes.

Plugs are especially suitable for applications that combine aerobic and anaerobic community or communities. In some embodiments, the structure of GMD can be suggested as a GMD sphere with two different layers, consisting of an inner core sphere and an outer covering shell. Since anaerobic microorganisms are sensitive to oxygen in the atmosphere, this strain should be immobilized inside the sphere of GMD. In the outer covering shell, aerobic microorganisms can be placed by immobilization. Both aerobes and anaerobes can do cross-talking by diffusion of chemicals they produce, but cells are physically entrapped in each side of the GMD sphere. Various parameters for tuning environment inside the GMD can be modulated such as diffusion path, porosity and tortuosity of gel matrices, etc.

Combinatorial Systems

Thus, useful for the practice of the present invention may be microfluidic devices (e.g. with compartments such as chambers or wells), droplets (e.g. beads or GMDs), or combinations thereof (e.g. combinations of channels with GMDs).

In some embodiments, this invention provides a novel combinatorial biosynthesis system by using a microfluidic device. This combinatorial biosynthesis system provides the cascade of continuous reaction centers. In a reaction center, different species of microorganisms are entrapped in the GMDs. At least two approaches are possible: use one bead with multiple microorganism strains; or use one microorganism strain per one bead, but beads are close together in a device to create a community, and optionally use controlled fluid flow to control communication among beads. In such a device, the reaction centers are connected with microchannels. This device takes advantage of the successive connections of reaction centers that are occupied by different strains of microorganisms. For example, compound X is synthesized from a substrate A and a substrate B. In this case, a complex reaction system comprising a reaction center 1 and a reaction center 2 can be provided. In a reaction center 1, species 1 producing a substrate A is deposited in a GMD. In a reaction center 2, species 2 producing a substrate B in deposited in a GMD. If these reaction centers are tightly incorporated with adjacent distance, but still physically separated in a microfluidic device, it is possible to make a continuous reaction system. Similar devices can be constructed for other synthetic schemes.

Furthermore, if one of the substrates is insoluble in the culture medium, e.g. hydrophobic (i.e. poorly soluble in water), it is possible to use a device having a separating layer that can selectively transport intermediates. Described herein are structures of devices for the biosynthesis via co-incubation of microbial communities, where the substrate is insoluble in the reaction media. There are many examples to enhance the water solubility of hydrophobic substrates via media engineering such as solubilization and dispersion in organic solvent media, biosynthesis in solid-phase media, or biosynthesis in eutectic media. However, it is still limited in single enzyme or single species biosynthesis.

Methods of Co-incubating Microorganisms

The devices of the present invention can be used in a method for co-incubating at least two different microorganisms such that at least one of the microorganisms performs a function differently than it would if the second organism was absent. For example, a microorganism may produce an incubation product that it otherwise would not produce when the second microorganism is present. Alternatively, a microorganism may not produce an incubation product that it otherwise would produce when the second microorganism is present. Alternatively, a microorganism may change the amount of an incubation product produced when a second microorganism is present compared to when it is not.

Incubation products include gases, liquids, or solids, or amorphous materials. Examples of incubation products are the small molecules or mono-, oligo-, or polymeric compounds, for example, bioenergy materials such as methane gas, hydrogen gas, biodiesel (fatty acids methyl- or ethyl esters), isoprenoids, probiotics, prebiotics, amino acids, sugars and sugar derivatives, glycoproteins, proteins (such as bacterial ice nucleation proteins), enzymes (such as heat stable polymerases, lipases, esterases), anti microbial agents, biologically active compounds and industrial compounds including natural products, fine chemicals, food additives (texturizing agent, sweetener), functional cosmetic materials (emulsifier, skin moisturizing compounds, antiperspirants, deodorants, microemulsions, skin sanitizing compositions), health-care compounds (personal-care emulsions, hair care compounds, antioxidants, anti-aging agents, anti-cancer agent, anti-hypochondria), biologically active polymers (such as polyhydroxybutyric acids), polyphenolic compounds (such as flavonoids), and xenobiotics (such as utilizing nitroaromatic compounds o-nitrobenzoate (ONB), p-nitrophenol (PNP) and 4-nitrocatechol (NC) as the sole source of carbon, nitrogen and energy). In addition, examples of products include molecules or processes involved in the production of bio-electricity. Applications include agricultural applications (such as production of insecticidal delta-endotoxins, soil fertility), food manufacture (fermentation processes and flavor enhancement, food safety), health care industry, fine chemical industry, drug development, bio-inspired energy industry, and medical/medicinal applications.

In another embodiment, during the co-incubating step, the first microorganism degrades or otherwise removes an external component in an amount that differs from what it would otherwise degrade when the second microorganism is absent.

Examples of external components which could be degraded or removed are the mono-, oligo- or polymeric molecules. They can be gases, liquids, or solids, or amorphous materials. Examples of gas include greenhouse gases such as $CO_2$ and methane. For example, polymeric compounds cellulose, hemicellulose, lignin, hydrocarbon (such as n-alkanes), aromatic compounds and their derivatives (such as polychlorinated biphenyls), halogenated organic compounds, polycyclic aromatic hydrocarbons, petroleum fuel compounds (including fuel-contaminated soil or marine samples), complex xenobiotics (such as insecticides, herbicides, or pesticides), sludge compounds (including heavy metals), organic wastes compounds (such as carbon disulfide, organic pollutants), waste water (such as self-contained water remediation), compost compounds, methane, ammonia, phenol and its derivatives, plastics, and heterocyclic compound of sulfur, nitrogen, and oxygen (such as dibenzothiophenene or dibenzofuran). These examples of compounds are applicable to the applications for bioremediation (such as heavy metal bioremediation and chemoattraction), bioaugmentation, bioenergy generation, reduction of natural contaminants, natural polymer reductions, agricultural applications (such as digesting grasses, coating of legume seeds, such as beans and peas).

The devices of the present invention can be used for drug discovery. Examples of isolation and cultivation of microorganisms from natural environments and drug discovery based thereon are disclosed in U.S. Pat. No. 7,011,957, which is herein incorporated by reference.

The devices of the present invention can be used for high throughput or capillary-based screening for a bioactivity or biomolecule similar to methods disclosed in PCT Patent Application Publication No. WO05010169A2, which is herein incorporated by reference.

The devices of the present invention can be ingested by a patient (human, cow, cat, dog or other animal). In some embodiments, the devices contain at least two microorganisms. In this embodiment, the first microorganism that produces (or produces more of) a therapeutic product in the presence, versus absence, of the second microorganism.

In another embodiment of an ingested product, the devices again contain at least two microorganisms. In this embodiment, the first microorganism degrades an undesirable substance in the intestinal tract of the patient in the presence, but not absence, of the second microorganism.

There are numerous other applications of the methods of the present invention. The methods can be used to look for combinations of microorganisms that naturally compete for a specific resource. In some embodiments, different microorganisms or microorganism populations can be forced to compete, not by mixing them where they can outcompete—e.g. simply outeat—one another, but by keeping them on separate fluxes of nutrients, which are still coupled. So, if one microorganism type can kill the other, it would get more nutrients. For example, bacteria may be used to kill fungi, fungi may be used to kill bacteria, viruses may be used to kill bacteria, etc. (Cowen and Lindquist, 2005, *Science* 309: 2185-2819). An assay could be performed to determine if the microorganisms have relatively increased the secretion of compounds that can kill the other microorganisms. Spatial separation in this instance may be important to decouple food and waste killing from a more selective killing. Such interacting microorganism colonies may be used to culture microorganisms that cannot be cultured by other means.

Commercial applications for microbes and microbial products include: a) bioremediation and bioaugmentation. Microbes have been put to use degrading organic chemicals through direct metabolism (in which the microbe uses the material for food or energy) and through co-metabolism (through which the microbe apparently gains nothing). They have also been used to carry out chemical transformations of inorganic materials in order to make those products less mobile or bioavailable in the environment. Applications include both in situ treatment (at the site of contamination) and treatment of waste streams in manufacturing settings; b) aids in mining operations. Bacteria are used in microbial enriched oil recovery and to extract precious materials from ore; c) Probiotics. Numerous probiotics products (consumables containing microorganisms that are thought to offer health benefits) are available to consumers today. Probiotics are occasionally used in medical settings as well; patients are sometimes administered a collection of probiotic microorganisms to head off colonization by *Clostridium difficile* after a dose of broad-spectrum antimicrobials; d) Manufacture of biofuel and other energy products. Bacteria are used to digest corn and sugarcane in the manufacture of ethanol, and researchers are exploring their use in transforming chemical energy into electrical energy in microbial fuel cells; e) Agricultural applications. Bacteria are used to digest grasses and other fodder to make silage, a feed material that can be stored for use during winter months when pastures are not available. Also, legume seeds, such as beans and peas, are often coated with nitrogen-fixing bacteria prior to planting to ensure the plants develop the proper nitrogen-fixing communities. A gene that encodes the insecticidal delta-endotoxin of *Bacillus thuringiensis* (a bacterium commonly called Bt) has been inserted into certain crops to improve insect resistance, and the bacteria themselves are sometimes sprinkled on crops to limit infestations. Although the neurotoxins produced by *Clostridium botulinum* have been a persistent problem in the food canning industry, the botulinum toxin is used in the medical and cosmetic (Botox) industries. Finally, the bacterial compound monensin is used to increase digestion efficiency in dairy cattle; f) Food manufacture. Microorganisms are put to work in food manufacture in many different capacities, including fermentation processes and flavor enhancement. Microbes are also significant in terms of food spoilage and food safety. There have been enormous and frequent food recalls due to microbial contamination; g) Industrial applications. Heat stable enzymes isolated from thermophilic bacteria, like Taq, lipase, esterases and others, have proven extremely useful in biotechnology; h) Wastewater treatment. This exploits the natural capability of microorganisms to degrade and recycle the essential elements on Earth. Millions of tons of organic and inorganic waste are treated annually, and more and more of the energy contained in this waste is recovered as biogas (methane). Important advances have also been made in recycling of sulfur and heavy metals; i) Microbial enhanced oil recovery is an efficient alternative to improve oil recovery, especially in mature fields and in oil reservoirs with high paraffinic content. Some bacterial strains could be co-incubated and can find utility in oil recovery applications and for the prevention and control of paraffin deposits. These strains include: *Pseudomonas aeruginosa; Bacillus lichenifonnis; Bacillus brevis; Bacillus polymyxa; Micrococcus varians; Micrococcus* sp. and *Vibrio* sp. (Almeida et al., 2004, *Engineering in Life Sciences* 4: 319-352); j) Application of microorganisms for the biodegradation of xenobiotics, especially xenobiotics that have accumulated in soil and water over the years, may include the use of *Burkholderia cepacia* and *Arthrobacter protophormiae*, capable of utilizing nitroaromatic compounds o-nitrobenzoate (ONB), p-nitrophenol (PNP) and 4-nitrocatechol (NC) as the sole source of carbon, nitrogen and energy (Jain et al., 2005, *Current Science* 89: 101-112); k) Other applications, such as manufacture of biodegradable plastics, green chemistry applications, and bacterial ice nucleation proteins are used in snow manufacture.

The methods can be used to identify microorganisms that secrete waste or other byproducts that could compromise the productivity of the other members of the community in a mixed culture.

In another embodiment, this invention could also be used to evolve strains of microorganisms that can kill undesirable strains of microorganisms. For example, an antibiotic-resistant strain of bacteria may be placed in chemical contact with another strain and the two strains may be stressed to compete for resources. Bacteria will evolve/adapt rapidly under stress, and it is possible that the second strain can evolve/adapt to kill the antibiotic-resistant strain. Analyzing the chemicals produced by the killer bacteria may provide new antibiotics/antibacterial molecules that will find utility in human medicine. In one example, sporulating *B. subtilis* are used, where sporulating cells induce lysis of un-sporulated cells to preserve resources. Microfluidics may allow performing these experiments in a high throughput format.

The devices of the present invention can be used to create an environment useful for testing the affects of environment changes on two or more populations of microorganisms. For example, after the systematic functional relationships of natural microorganism consortia are confirmed (e.g. symbiotic or syntrophic relationships), those relationships can be reproduced in the microfluidic devices of this invention. For example, a microbial community that degrades cellulose can be analyzed to understand the structure of the community, characteristics of each community member, functional correlation between members, and synergistic reactions in the community. Then, this community can be mimicked with different species that perform the same functions with better performance (e.g. higher enzymatic activity, better thermal stability, etc). In this process, it is possible to optimize the artificial community by creating synthetic community with different origin. One could thus make the "artificial symbiosis" system based on the mimicry of natural symbiosis. The major difference between artificial symbiosis and natural symbiosis is that one can replace the strains in a community with more powerful and cooperative strains. Such an artificial community may resemble an enzyme cascade in a whole cell of a microorganism.

Examples of suitable systems include: 1) a community which performs cellulose degradation and alcohol fermentation (community members would include: cellulose solubilizing species (anaerobe), cellulose degrading species (anaerobe), oxygen consuming species (aerobe), oligosaccharides saccharifying species (aerobe, anaerobe), alcohol producer (anaerobe)); 2) a community which performs cellulose degradation and methane generation (community members could include: cellulose degrading species (cellulose→oligosaccharides), oligosaccharide degrading species (oligosaccharides→acetate), and methane generating species (acetate→methane)); and 3) a community which performs hydrocarbon degradation and oxidation (community members would include: hydrocarbon degrading species, acetate generating species, methane and methanol generating species, pH tuning species etc).

In another example, lipase activity may be induced. Lots of bacterial lipases have shown their optimum catalytic activity in the alkaline condition, whereas they are inactivated in acidic condition. To mitigate this, a bacterial cocktail of strain A (lipase producing bacteria in alkaline conditions) and strain B (alkali producing bacteria) could be placed in separate compartments in a microfluidic device of the present invention. The compartments could be linked by communication channels containing lipase assay chemicals (e.g. rhodamine B) and acids (making acidic conditions). When the two-strain-community (A-B) functions, rhodamine B color will be changed because lipases produced by strain A can work in the neutralized (or alkalified) region by the strain B. In this way, a community comprised of a lipase producing species and a species which lowers the pH of the local environment could be used to produce lipase activity.

In another example using lipase, the lipase production via yeast (e.g. *Candida rugosa*) can be inhibited by the presence of antifungal agent (e.g. cycloheximide). Interestingly, cycloheximide can be degraded by alkali over pH 7.0. Therefore, strain A (lipase producing yeast) and strain B (alkali producing bacteria) are placed in different compartments of a microfluidic device of the present invention. These compartments are linked via a communication channel containing lipase assay chemicals (e.g. rhodamine B) and cycloheximide. When the two-strain-community (A-B) functions, the color of rhodamine B will be changed after the degradation of cycloheximide by the alkali producing strain B. If a strain B which degrades the cycloheximide enzymatically is identified, then strain B can be replaced.

In yet another example using lipase, bacterial lipase cannot work in the presence of lipase inhibitor (e.g. tetrahydrolipstatin or orlistat). In this case, strains A (lipase producing bacteria) and B (lipase inhibitor producing bacteria) are separated into two compartments on a microfluidic device of the present invention. Then, this device is placed on the agar plate containing lipase assay chemicals (e.g. rhodamine B) and lipase inhibitors. When the two-strain-community (A-B) functions, color of rhodamine B will be changed after the degradation of lipase inhibitor by the strain B.

In an example using antibiotics, it is possible that the combination of two antibiotic-resistant bacteria can make other bacteria survive in an agar medium containing two antibiotics with different mode (e.g. β-lactam and aminoglycoside). For this example, the *E. coli* strain would be placed in the communication channel containing antibiotics, penicillin G and kanamycin. Strains A (β-lactamase producing) and B (kanamycin-modifying enzyme producing) would be place in separate communication compartments. When the two-strain-community (A-B) functions, *E. coli* on the same region can grow because β-lactamases and kanamycin modifying enzymes will degrade the penicillin G and kanamycin by secretion. In this case, growth profile (growth rate of *E. coli* over time) should be traced, instead of clear zone.

This invention takes advantage of the discovery that a defined spatial structure is required for the stable coexistence of multiple bacterial species in a synthetic community. A community of two or more interacting populations may be created by using a microfluidic device to control spatial structure and fluid communication (e.g. chemical communication) between the populations. For example, a community of two or more strains (species, etc.) of wild-type soil bacteria with syntrophic interactions can be created by using a microfluidic device to control spatial structure and chemical communication between the colonies (microcolonies).

In one example, a microfluidic device may be used to localize individual types of microorganisms (e.g. discrete bacterial species) into individual culture compartments (e.g. chambers, wells) separated from a microfluidic communication channel by a nano-porous membrane (FIGS. 1-4). In those embodiments when a microfluidic device is used, this device spatially localizes each type of microorganisms (e.g. discrete bacterial species) while allowing fluid (e.g. chemical) communication among the types of microorganisms. Control experiments may be performed, if desired, to verify that the microorganisms remain confined and that chemicals are exchanged by diffusion through the communication channel(s). This microbial community is stable only when the microcolonies are separated by a certain distance, such as, e.g., hundreds of micrometers, but unstable when the microorganisms are cultured together or separated by longer distances. A mathematical model can be developed to suggest how spatial structure can balance the competition and interactions within the community, even when the rates of production and consumption of nutrients by species are mismatched, by taking advantage of nonlinearities of these processes. These devices may support the growth and co-incubating of any desired number of microorganisms, thus providing for the co-incubating of a class of communities that require spatial structure for stability. Controlling spatial structure may enable harnessing the function of natural and synthetic multi-species communities in the laboratory.

It is contemplated that the present invention is suitable for practice with microbial communities that are either mixed communities or spatially structured communities. Some microbial communities could be unstable over long times when mixed, but still functional/stable enough over short times. Thus, for purposes of the present invention, even mixed communities are considered spatial communities when there is at least one aspect that benefits from spatial control of the community, i.e. when they are relatively more stable under spatial control. Such aspects of spatial control may include, for example, increased stability, functionality, etc. Also, in terms of spatial structures, the present invention allows some degree of intermixing since it would be beneficial even just having a gradient, rather than abrupt transition, from one composition of microbes to another composition of microbes.

FIG. 1 illustrates one example of the devices of the present invention. In this embodiment, the device has at least two layers, referred as "lower" and "upper" for simplicity. The lower layer contains various sizes, shapes, and separation distances of structure. In this lower layer of a device, different microorganisms, species or strains can be individually inoculated within their own confined space. In the upper layer of the device, various sizes and shapes of communication means can be structured, which connect the culture compartments (e.g. wells) of the lower layer. These communication means mainly serve the purpose of transporting chemical, biological, and/or physical information and/or substances between the different microorganisms. The communication means can be, e.g., communication channels in a variety of sizes, shapes, or forms. The actual number, size, and dimensions of the channels may be varied as desired (FIG. 1), to provide a certain amount of communication between the compartments with microorganisms. For example, the communication means can be small channels that will allow flow of liquid between the two microbial compartments. In some embodiments, the flow of fluid between the two microbial compartments may be directional (from one microbial compartment to another). Alternatively, or in addition, the communication means may provide only the possibility for diffusion of molecules or compounds between the two microbial compartments, without any flow of liquids between the microbial compartments. Between these two (lower and upper) layers, a barrier may be positioned. Suitable examples of a barrier may include a 0.1 µm pore sized polycarbonate (or other types of materials) membrane. The polycarbonate membrane permits the chemical diffusion of small molecules. Thus, the device contains an upper layer (for exchange of released chemicals) and a lower layer (to be inoculated with various strains of microorganisms, e.g. bacteria). The upper and lower layer are separated by a membrane or other barrier structure that would enable exchange of chemical information between the upper and lower layer, but would prevent the movement of intact/whole microbial cells from the lower layer to the upper layer. In one example, the upper layer contains a microchannel that allows weak flow of media (or reaction solutions) to go through at the end of the channel, and then eventually pass through the 0.1 µm membrane. The upper layer could either have no flow (transport by diffusion only) or could have flow such that compounds released from one lower layer compartment are transported to other compartments downstream. The procedure of chemical (and/or physical, biological) communications is as follows: small molecules diffuse from the culture compartments in the lower layer, move to communication channel in a upper layer, and are then transferred to other culture compartments in the lower layer. In this system, it is possible to modulate the chemostat-style culture with longer operation times by supporting some nutrients. Furthermore, one can use the upper channel as a pipeline for fluctuating the amount of nutrient being delivered, to look at responses.

The type of system shown in FIG. 1 could be implemented using various other geometries. The key components are 1) chambers which contain cells which are physically separated from one another 2) chamber separated by a membrane or structure that acts as a barrier to cells but enables chemical exchange. Other systems which could be used for similar purposes include: 1) gel beads with different types of microbes spatially located in different regions of the bead; 2) a chamber containing a microbe covered with either a layer of gel or a membrane and other type of microbe placed on top of the gel/membrane.

This method can be applied to culture the microbial communities comprising two or more different species. In this system, structural geometry and the chemical communications provide the interactions between species, which promotes the co-incubation of functional microbial communities depending on their enzymatic reactions for the stable coexistence.

FIG. 1 illustrates how each culture compartment (e.g. well) can be connected with various 3D spatial architectures. The device therefore allows coupling of multiple (two, three, or more) microorganisms or communities of microorganisms. Especially, this concept can be effectively applied to microbial communities showing synergistic interactions of degradation, synthesis, and modification of natural compounds.

The structure of the compartments can be tuned and adjusted depending on the microbial species or culture types. The structure of culture compartments in the lower layer of a device is various and it may be, for example, of a small patchy well type or a long stripe type. The structure of a communication channel in the upper layer of a device should contain the supporting posts, which is aligned with the structure of culture wells in a lower layer. The structure of the compartments may be able to provide cultivability of microbial communities from natural sources, even presumably the uncultivable microbial communities. The number of culture compartments per any device or unit device may vary.

The individual culture compartments can be functioning as individual continuously stirred tank reactors (chemostats)

that are stirred by active flow or diffusion. Coupling among such culture compartments by fluidic connections or other methods that provide chemical exchange can provide a platform for implementing microbial communities.

The concept of culture compartments can be further developed by exchanging or extending layers to the lower layer or upper layer. For example, the thin agar layer containing microorganisms can be replaced with the lower layer. In this case, the agar gel provides a reduced flow but permeable path to microorganisms. When this gel layer is attached with various shapes of upper channel layer, communication channels in an upper layer can provide the concentration profiles. This device setup can be applied to investigate chemotaxis of microorganisms by switching the nutrients with the inhibitors (or chemorepellents). Furthermore, one can analyze how microorganisms can adapt to periodic fluctuations of chemicals, how microorganisms evolve by themselves against the environments in the periodic life cycle, and how microorganisms die as the spatiotemporal changes.

In one aspect of the invention, provided are devices and methods that are useful for co-incubating discrete populations of microorganisms, and for the detection and/or screening of discrete populations of microorganisms. This invention could also be use to perform assays by forming random groupings of cells and screening in the sense of replacing/adding one member to an existing group to modify and/or improve a desired function.

Once microbial communities have been formed, functional screening can be used to determine if any of the communities exhibit functions of interest. Control functional screens could be done on droplets containing only a single member of the community in order to distinguish community functions from those functions which only require single species.

Screening for functions could be done in the following ways: 1) Deposit the droplets containing communities onto gel surface which contains an indicator for a specific function. For instance, if the gel surface changes color around one of the droplets, then that droplet contains a communities which performs that function. A similar test could be run for communities in compartments such as microwells. The gel containing an indicator could be placed over the wells. The gel directly above the active wells would indicate function through color change or change in opacity or clearing zone around growing cells (as in an antibiotic test); 2) Add an indicator (such as fluorescent indicator) to the droplets and use established techniques such as FACS or flow cytometry to determine which droplets perform the function; 3) A self-sorting mechanism could be used to perform functional screens. If the function has an output that would enable the active droplets to segregate from the inactive particles (through changes in response to an electric or magnetic field, to changes in density, to resistance to chemical degradation, etc.). The self-sorting mechanism could also involve breaking through a barrier. For instance, droplets could be deposited on top of a thin plastic film, and those droplets that are able to degrade the film and fall through have the function of being able to decompose the material in the film; 4) The function of the community in a droplet or in a microwell could also be recorded on a surface. The droplets could be placed on a surface and left to incubate. The surface which is in contact with the droplet would then have a residue that would be associated with the activity of the droplet. Techniques such as MALDI mass spec, SIMS, or other techniques that are able to scan a surface to find specific chemicals could be used to find the communities with a specific function. Useful aspects that include microengraving methods for rapid selection of single cells producing antigen-specific antibodies can also be found in Love et al., 2006, *Nature Biotechnology* 24: 703-707.

Numerous examples of functional communities that can be identified and screened according to the present invention can be provided. Some examples of (artificial) functional communities are listed below. These functional communities include two or more of: producer P (antagonist), receiver R (sensitive to antagonist), sensitive to antagonist strain S; and resistant helper R (resistant to antagonist): 1) Antibiotic producer (P), sensitive strain (S), antibiotic resistance (R); 2) Quorum sensing strain (P), QS sensitive strain (S), quorum quencher (R); 3) Bacteriocin producer (P), sensitive strain (S), protease/peptidase producer (R); 4) Peroxide producer (P), sensitive strain (S), scavenging strain (R); 5) Acid producer (P), sensitive strain (S), acid decomposing strain (R); 6) Alcohol producer (P), sensitive strain (S), alcohol degrading strain (R); 7) Surfactant producer (P), sensitive strain (S), surfactant decomposing strain containing lipases/esterases (R); 8) Sugar alcohol producer (P), Sugar alcohol sensitive; disable to use sugar alcohol (S), sugar alcohol resistant; enable to use sugar alcohol (R).

The apparatuses and methods of the present invention can be used to perform functional screens for the identification of microorganisms based on their functional properties, such as enzymatic activity, secreted molecules, etc. The devices of the present invention are seeded with a plurality of microorganisms, which are compartmentalized in respective confined spaces. A high enough seeding density is needed so that communicating/adjacent compartments are likely to be occupied; at the same time, the seeding density is low enough so that these compartments are not occupied by multiple microorganisms. A functional assay is then performed and the candidate microorganisms are identified. These functional screens can also be performed in a high throughput fashion. In different embodiments the device may be added into a solution, or placed onto a substrate or bacterial culture.

If this method is used to select for individual microorganisms out of many, the barrier is preferably re-sealable, so once the organism that breached it passes through, the barrier reseals itself to prevent other organisms from escaping The apparatuses and methods of the present invention can be used for co-incubating two or more populations of microorganisms. Maintaining interactions among microbial populations can be performed on a microfluidic chip, where the microorganism are localized in some areas and allowed to directly or indirectly interact through barriers. Examples or suitable barriers include fluid or gas or gel or solid materials, such as droplets or membranes. In an apparatus, the microorganisms may be confined by barriers with pores small enough to be not permeable to bacteria, but large enough to allow diffusion of molecules and flow of fluid. Several architectures can be used, including multilayer architectures. Ideas resembling chemostats and continuously stirred tank reactors can be implemented on a microfluidic chip using these methods. Gels may also be used to trap microorganisms and allow transport of molecules.

An important concept in the devices and methods of the present invention is the ability to separate individual microbes by intermediate distances. If microbes are too close (mixed together such that there is no spatial structure, physically touching, not immobilized, immobilized but only micrometers apart) then the microbes will directly compete (either through competition for shared nutrients, one microbe releasing waste or a chemical that inhibits the growth or activity of another microbe). By physically separating the microbes over space, competition is reduced. However, communities' functions may involve the exchange of chemical between different microbes. Therefore, although the microbes should be separated to reduce competition, they also should be close enough such that they can effectively exchange chemicals. The distance over which a group of microbes can effectively communicate with another group of microbes through diffusive gradients has been estimated to be approximately 25 microbe lengths. Generally, the spatial structure/separation distance between microbes should be on the order of hundreds of µm. Generally, millimeter and centimeter scale separations are too large. Effective intercellular communication distances can also be determined by methods such as the relative time constants for secretion and diffusion of molecules (Francis and Palsson, 1997, PNAS, 94: 12258-12262).

FIG. 3: illustrates the concept of how a synthetic community of three bacterial species requires spatial structure to maintain stable coexistence. FIG. 3a: a schematic drawing of the wild-type soil bacteria and their functions used to create a synthetic community with syntrophic interactions. FIG. 3b: graphs show the survival ratio of each species (N/No) as a function of time when cultured in well-mixed conditions in a test tube in nutrient-rich (left) and nutrient-poor (right) media, indicating instability of the community under spatially unstructured conditions. FIG. 3c: a schematic drawing of the microfluidic device used to stably co-incubate the three species by imposing spatial structure with culture wells and a communication channel.

FIG. 4 illustrates how the stability of the community requires communication among microbial species, as explained below. FIG. 5 illustrates the concept of how a synthetic community only coexists at intermediate separations, as explained below.

In some embodiments, stencils could be used to control the loading of cells into an array of compartments (e.g. microwells) on a device. An example of this method is schematically shown in FIG. 2. The device would consist of an array of microwells on a lower layer, a membrane, and an upper layer which would contain fluidic connections for sets of microwells (i.e. a set of 4 microwells on the lower layer would all be connected to the same channel on the lower layer creating a community of the cells in the 4 microwells). Stencils could be used to cover a portion of the holes on the upper layer during seeding. For example, if communities of 4 connected microwells (i, ii, iii, iv) are generated, a stencil could be used to cover all of the wells ii, iii, and iv on the chip and cells could be loaded into well i. The stencil could then be moved to enable access only to well ii and another type of cell could be loaded into well ii. In this way, specific cell types could be loaded into specific wells in each set of wells, and therefore a large array of community could be seeded each containing the same types of cells (i.e. every set of 4 wells has 1 well with species A, 1 well with species B, 1 well with species C, and 1 well with species D). A variation on this type of loading would be to load all of the wells i, ii, and iii on the array with a preset combination of cells and then to load well iv with a random strain of cell. For example, each community may contain *Pseudomonas aeruginosa, Bacillus cereus, Streptomyces coelicolor*, plus one additional community member randomly seeded from a mixture of soil microbes. In this way, one could screen for how the addition of a new community member influenced the function of a specific community of microbes.

The following mathematical model is provided to better understand the role of spatial structure and is not intended to limit the present invention. FIG. 6 is a mathematical model of a two-species syntrophic community. As indicated in FIG. 6 and in the text, individual planes represent: the rate of consumption; the concentration of nutrient B at species alpha, $[B_{alpha}]$, the rate of production of nutrient A; and the minimum rate of consumption of nutrient A. FIG. 6a: colony alpha produces nutrient A and colony beta produces nutrient B. Both nutrients establish gradients over a distance L (m), which is the distance between the centers of colonies alpha and beta. FIG. 6b: 3D rate plot of consumption of A (plane) varied with L. FIG. 6c: 3D plot of $[B_{alpha}]$ (plane) varied with L. FIG. 6b-i, 3D rate plots and 2D sections show the state of the community when colonies of species alpha and beta are separated by small (d, g), intermediate (e, h), and large (f, i) L. The steady-state concentration of nutrient A occurs where the consumption and production curves intersect at the given concentration of nutrient B. FIG. 6d-f: 3D rate plots from a Class II community predict a non-zero steady-state only at intermediate L, indicating that the synthetic community experimentally tested here is Class II. FIG. 6g-i: 2D sections of representative production and consumption curves for Class I, II and III communities.

While the exchange of essential nutrients between the colonies is considered herein, these results should apply for the exchange of other diffusible molecules that regulate the functions of neighboring colonies. This model considers a bacterial colony of species alpha that produces nutrient A and a colony of species beta that produces nutrient B. Nutrients A and B diffuse between colonies of species alpha and beta, which are separated by distance L (m). The production function is known to be nonlinear: onset of production typically occurs above a critical concentration of nutrients, and production saturates or is even inhibited at high concentrations of nutrients. This nonlinear dependence of production of nutrient A on the concentration of both nutrients was approximated as the product of two Hill functions:

$$Production_{A,alpha} = \frac{\partial A_{alpha}}{\partial t} \qquad (1)$$
$$= \frac{k_1 * A_{alpha}^3 * (B_{alpha}(L))^3}{(k_2 + A_{alpha}^3) * (k_3 + (B_{alpha}(L))^3)} * S_{alpha}(A_{alpha}, B_{alpha}, t)$$

where $k_1$, $k_2$, $k_3$ are rate constants, L is the distance between the colonies (m), $N_{alpha}$ is the size of colony alpha (number of cells), t is time (s), [A] is concentration of A (M). For simplicity, a model in which species beta is a constant source of nutrient B is considered (FIG. 6, vertical planes in c, d, e, f) at a fixed ratio of species populations $S_{alpha}/S_{beta}$, where $S_{alpha}$ is the number cells in colony alpha and $S_{beta}$ is the number cells in colony beta (FIG. 6). $S_{alpha}$ and $S_{beta}$ are taken to be constant, assuming that the number of cells changes slowly on the time scale of metabolic activity, as could be expected for many strains of soil bacteria that are slow growing. The same conclusions are obtained for the more general model using analysis of nullclines. The production of nutrient A calculated with equation (1) is shown as the curved gray plane in FIG. 6.

Each species also consumes both nutrients; this consumption is taken to be linear for simplicity, where the rate of consumption of nutrient A by colony alpha is defined as $$Consumption_{A,alpha} = -\frac{\partial A_{alpha}}{\partial t} \qquad (2)$$
$$= k_4 * A_{alpha} * S_{alpha}(A_{alpha}, B_{alpha}, t)$$

and the rate of consumption of nutrient A by colony beta is defined as $$\text{Consumption}_{A,beta} = -\frac{\partial [A]_{beta}}{\partial t} \quad (3)$$
$$= k_5 * [A_{beta}](L) * S_{beta}([A]_{beta}, [B]_{beta}, t)$$

The total consumption of nutrient A is take as the combined total of equations (2) and (3) and is shown as the dark gray flat plane in FIG. 6b, d, e, f. The shapes of consumption and production curves of glucose by Pc were confirmed experimentally. Nonlinearity must be present for spatial effects to be observed. The concentrations of $A_{beta}$ and $B_{alpha}$ are a function of L such that $[A]_{beta}=[A]_{alpha}$ and $[B]_{alpha}=[B]_{beta}$ when species alpha and beta are close together, and $[A]_{beta}=[B]_{alpha}=0$ when they are infinitely far apart, e.g. mimicking the profile of a diffusive gradient connecting species alpha and beta. $S_{alpha}$ and S are functions of [A] and [B] over time.

The system is stable at a distance L only when the combined consumption rate of a nutrient is matched by the production rate. This criterion is only met when the three surfaces for $[B]_{alpha}$, production of A, and consumption of A in FIG. 6 cross at a non-zero point. As L is increased, two effects compete: the consumption of nutrient A by species beta decreases (FIG. 6b), and $[B]_{alpha}$ decreases (FIG. 6c). The spatial dependence observed in FIG. 5 is recapitulated in this model. For small L, $[B]_{alpha}$ is high, but mutual consumption exceeds production and the criterion for stability is not satisfied (FIG. 6d). For larger L, both $[B]_{alpha}$ and the consumption rate decrease (FIG. 6e), and a stable steady state appears. The nonlinearity (saturability) of the production curve is critical in this model: species alpha is insensitive to a decrease in $[B]_{alpha}$ but sensitive to a decrease in the consumption of nutrient A. No stable steady state is found at very large L (FIG. 6f): while the consumption rate of nutrient A by species beta becomes insignificant and the total consumption rate approaches the rate of consumption of nutrient A by species alpha only (FIG. 6, plane labeled consumption from alpha only in 6b, straight line with lowest slope in g, h, and i), $[B]_{alpha}$ becomes so low that it becomes limiting.

Space affects the interaction of community members in important ways. First, when colonies are too far apart, the concentration gradients of nutrients they produce approaches zero due to diffusive loss, resulting in colonies that are essentially isolated. Second, when colonies are too close, they directly compete for nutrients. Both the intrinsic rate each species performs its function and the transport dynamics of the system determine the relative contribution of diffusive loss and interspecific competition on the community.

This model predicts three classes microbial communities (FIG. 6g-i) with obligate interactions. A "Class I" community is stable even in a well-mixed environment (FIG. 6g) as well as at intermediate separations (FIG. 6h), because production rates are sufficiently high to accommodate consumption by all species. However, a Class I community is not stable beyond a maximum separation where metabolic coupling is lost (FIG. 6i). A "Class II" community is not stable when colonies are well-mixed or too close, because consumption exceeds production (FIGS. 6d and g). A Class II community is one that requires intermediate spatial separation of the species in order to form a stable/functional community. As the species become spatially separated, interspecific competition is reduced, and the community becomes stable (FIGS. 6e and h) until the maximum separation where metabolic coupling is lost (FIGS. 6f and i). Class II communities require spatial structure for stability; the synthetic community described herein is Class II. A "Class III" community is not stable at any separation distance, because the distance at which the colonies are metabolically decoupled is smaller than the distance at which cross-consumption is sufficiently reduced (FIG. 6g-i).

Several Class I communities have been characterized and cultured, but the number of natural communities vastly exceeds the number of communities cultured in the laboratory. Metabolic requirements for a Class II community are less restrictive and one may expect them to occur more frequently. It remains to be established whether many natural communities are Class II; if so, they would not be cultivable by traditional methods but could be cultured by methods that control spatial structure, such as microfluidic devices presented herein. Using the devices and methods of the present invention, it is possible to examine the spatial structure and transport in natural environments, to understand how communities of microbes interact and perform community-level functions in natural ecosystems, and to understand how species diversity of microbial communities is maintained. In addition, control of spatial structures in the laboratory may be used to test known microbial strains for new functions, to discover communities that perform various (desired or not) functions, to stabilize natural microbial communities and harness their functions, or create synthetic communities with new functions. Once a community is identified, it can be scaled up and multiplied, to produce microbial amounts sufficient for desired applications, e.g. in numbers that can be useful for antibiotic production or environmental remediation, for running reactions by exchanging metabolites among types of microorganisms, etc.

In one aspect, this invention may be thought of as a three-dimensional matrix of co-incubating systems that includes a variety of devices suitable for confinement and/or separation of microorganisms in the first dimension, a variety of microbes and microbial communities in the second dimension, a variety of applications in the third dimension. Such a 3D matrix provides for any three-dimensional interactions, i.e. any device with any community with any application is possible according to the present invention. As well, the interactions may involve more than one device, community, and application. Suitable examples of a variety of systems, devices, microorganisms, microbe communities, and applications, can be found herein.

Since community viability and function relies on an approximately constant spatial structure (microbes or immobilized, structure is not fluid), one might imagine that simply spreading mixtures of microbes onto agar plates may be able to provide such structure. However, using the devices and the methods of the present invention has at least the following advantages: 1) culture compartments can precisely define the structure of community. It is likely that communities require a specific range of spatial separation (e.g. microbes 1 and 2 have to be between 100-500 μm apart to form a functional/viable community). Randomly generated structures, where the distance between the microbes in random and the number of microbes in a given area is random, such as spreading microbial mixture on an agar plate, will result in a very small percentage of communities with microbe 1 and 2 100-500 μm apart with no other microbes nearby. Estimates such as how far apart community members should be based on chemical production and consumption rates as well as transport rates should be able to predict approximate spatial structures that will enable community function/viability. Thus, culture compartments can be created that only try a small set of possible geometries, therefore greatly increasing the odds of finding a functional community; 2) culture compartments have the ability to limit growth. For example, if two microbes are spread onto an agar plate, the microbial colonies may continue to expand until they occupy the entire plate. Therefore if one of the microbes grows much more rapidly than the other, the spatial structure of the community (two microbial colonies 200 µm apart) will not be maintained over time). Culture compartments could have finite volumes and barriers which would inhibit the extent of growth of a microbial colony. In this way, fast growing colonies will only grow to a finite and controllable size, allowing for slow growing microbial colonies to form.

Spatial structures also enable communities of cells to tolerate one another. For example, a community of cells "A" and "B" may not be able to survive in a mixed culture, however if they are placed in a structured space then the competitive interactions would be decreased. The cells might not have positive (symbiotic) interactions, but space would enable them to both survive and tolerate being near one another. Tolerance could lead to community level functions as the cells in the community could perform complimentary functions that would combine to enable higher level functions (such as multi-step degradations, multi-step synthesis, induction of specific cell behaviors, etc.).

Stochastic confinement can also be used in combination with screening for community functions. By taking a sample containing multiple species of microbes all mixed together, generating small volumes plugs (stochastic confinement) can be used to separate this mixture into discrete volumes each containing a single microbe. In this way rare and slow growing microbes can be separated from fast growing and ubiquitous microbes. After confining the microbes, they can be cultured (since inter-species competition is reduced) and the culture inside each droplet could benefit from stochastic confinement effects such as the accumulation of released molecules which could speed the transition out of the lag phase. The separated microbes could then be seeding into communities either by combining droplets or loading each droplet into a separate microwell with structures that would enable the exchange of chemicals between the wells. Confinement effects are again important for the community structure, as confinement will enable the accumulation of released molecules (decreased dilution) which will increase the flux of chemicals between species and may increase the overall rate of community function. Preincubation of individual microbes in confined droplets before seeding into community structures would also enable rare microbes to increase in number (which means they could be incorporated into more communities) and also would enable the seeding of replicate communities by splitting the droplet into multiple droplets containing the same microbe before seeding the community.

One advantage of the devices, systems, and methods of the present invention is that release of compounds from microorganisms is highly dependent on culturing conditions. For example phosphate levels, temperature, nutrient availability, and other environmental conditions, all influence the production and release of various metabolites. This invention thus enables the screening of media conditions and concentrations of additives both for communities, common species, and rare species of microbes. Thus, if desired, it may be possible to grow certain communities for much longer if some nutrients are provided, or it might be possible to fluctuate the amount of nutrients being delivered, to look at corresponding responses.

Various aspects of assays that can be used in the practice of the present invention can be found in Balagadde et al., 2005, *Science* 309: 137-140 (long-term monitoring of bacteria undergoing programmed population control in a microchemostat), and in Groisman et al., 2005, *Nature Methods* 2: 685-689 (microfluidic chemostat for experiments with bacterial and yeast cells).

There are numerous applications for encapsulated microorganisms in GMD. For example, certain bacteria accumulate precious metals or radioactive contaminants or heavy metal contaminants. Screens can be devised that select for such types of bacteria that tend to accumulate heavy metal elements. Different bacteria can be encapsulated into gel beads (e.g., a library of mutants of one species, or a combinatorial library of mutants of several species to create communities). The gel should be chosen to have similar density to the density of encapsulated bacteria. These beads are then exposed to a sufficiently large volume of solution than contains salts of the heavy element that should be collected (accumulated). The density of the solution is adjusted so the beads barely float. The volume of the solution is adjusted to provide for separation of floating beads from sunken beads. If bacteria accumulate the heavy element significantly, the beads would sink. The sunken beads are collected, and the bacteria from these beads are sequenced as candidates for element accumulation. The screen may be optionally repeated. The screening threshold can be adjusted by simply increasing the density of the fluid to which the beads are exposed; in this case, the beads would have to accumulate more of the element to sink in it.

Once the strain (or the community) that accumulates metal is identified, these microorganisms can be encapsulated in beads that contain magnetic particles, can be dispersed in the environment. Let them soak up the heavy elements, then use a magnet to collect the product. Bacteria that metabolize these elements into insoluble derivatives would be especially useful; each bacterium then could have a product of accumulated element (e.g. metallic gold or uranium, or a piece of insoluble strontium sulfate).

This is potentially more efficient than trying to accumulate a protein-element complex. Also, it could potentially require a combination of bacteria—one accumulates the other produces the precipitating agent. If the protein-element complex is found, then the protein could be used outside of bacteria, if it is economical, but accumulation of metabolized products may be easier. Some secondary concentration by using predators that would eat the bacteria (even without beads) could be useful.

The present invention contemplates the use of 2D methods for encapsulation of cells (FIG. 9). The methods for encapsulating large numbers of cells are similar to sequential merging of reagents to plugs flowing in a 1D microfluidic channel (straight channel). Examples of micro cell encapsulation and its hydrogel-beads production using microfluidic device are shown in Shintaku et al., 2007, *Microsystem Technologies* 13: 951-958; however, here the cells are introduced into a 2D channel (width of channel much larger than width of cell) and the cells flow through regions in which various reagents are applied to the cells. The 2D channel should be approximately the similar in height to the cells such that the cells flowing through the device form a monolayer (FIG. 9).

In the 2D devices, cells or plugs containing cells enter a region in which the width of the channel gets much larger than the width of the cell. In the top of this wide region is a membrane or structure with small pores. On the other side of the membrane are channels which deliver reagents to the cell/plugs. For example, as the plugs pass by the region of reagent 1, the plugs come into contact with reagent 1 passing through the pores of the membrane and pick up reagent 1. In this way, the plugs can pass through multiple regions of reagent of multiple layers of reagents can be deposited. Key parameters in the design of the 2D device will be 1) flow rate of cells 2) pressure drop in the reagent channels (porosity of membrane, size of pores, length of pores (in direction of flow), width of reagent channel, width of cell channel) 3) width of reagent region 4) number of reagent regions. The amount of time spent in each reagent region and the pressure drop in the reagent channel will determine the amount reagent deposited on each cell. A 2D such as the one above could be much wider (e.g. hundreds to hundred thousands of cell lengths wide) to enable a large scale process of cell encapsulation. Reagents added to the plugs/cells could include gel components, drugs, screening targets, other types of cells, cell extracts, genetic material, magnetic particles, antibodies, and emulsifiers.

The 2D method is useful for high throughput/larger scale applications. A comparable 1D method could also be useful for some applications. In some embodiments, two or more 2D devices may be stacked in multiple layers to make 3D devices to increase throughput.

An alternative encapsulation method could involve the formation of plugs using a multiple inlet junction to mix several fluids together. Additional layers could be added the plugs by flowing them past subsequent multiple inlet junctions. For example, a plug could pick up a layer of gel by flowing past a junction with an aqueous stream of $Ca^{2+}$ solution and an aqueous stream of alginate. The two streams would mix and surround the plug, creating a gel layer around the initial plug. In preferred embodiments the surface tension at the interface of the carrier and the first plug fluid is higher than the surface tension at the interface of the second plug fluid and the carrier.

For such plugs containing multiple layers of fluid, some of the fluid layers will contain cells or a single cell and some of the layer will act as a barrier to physically isolate each cell layer. This would enable layers of cells to exchange chemicals but would prevent mixing of the different cell types. The barrier layer thickness, porosity, transport rate, permeability, material can be optimized to control the spacing between the layers of cells (as some cell combinations will require specific separations). The order of layers, volume of layer, shape of layer, inoculum size, and the addition of other layers containing assay/detection reagents, nutrients, metabolites, will influence the overall viability and function of each layer and the community as a whole.

In some embodiments, it is possible to combine the GMD and a microfluidic device. In detail, species A and B can be entrapped in the GMD with appropriate sizes and shapes, respectively. On the other hand, a microfluidic device provides a bioreactor that GMDs are packed and interacts to each other. Several microfluidic devices will be connected, which contains different GMDs as the cascade of microfluidic reaction centers. Once the GMD is packed into the microfluidic device, GMD cannot be secreted out of the device. After GMDs containing each species of A and B are prepared, each GMD is packed into the microfluidic device A and B, respectively. In this system, once species A entrapped in a GMD in a microfluidic device A produces a precursor A, then this secreted out and move to microfluidic device B. Then the precursor molecules are moving into the GMD bearing species B in a microfluidic device B, and glycosylation reactions are performed by the enzymatic reaction of glycosyl transferases. Then the final products will be secreted out of device B to next stage.

The GMD-based co-incubation in a microfluidic system can be a new model system for a variety of applications, for example for novel natural products discovery, for one or more of the following reasons: 1) GMD-based co-incubation makes communication among some strains to be more stable compared to bulk co-incubation. In most cases, co-incubation of different strains makes one strain less viable. Physical confinement by the GMD has been proved to maintain the viability of microorganisms; 2) microfluidic system can produce novel natural products with shorter culture time and smaller volume; 3) co-incubation in microfluidic devices enables to study the importance of spatial structure where microorganisms interact with each other.

Confinement of microorganisms using GMDs, compartments, or in any other ways according to the present invention, has advantages for screening rare cells/communities. It is known that some strains of microbes will not initiate growth or some cellular functions unless cell density is above a minimal threshold. It is also possible that although the process is occurring, the rate at low cell densities may be so slow that it would take weeks or months to observe growth or the function. Therefore, by placing single cells in very confined spaces with small volumes it is likely that they will initiate high density processes and that many processes will have increased rates. This is especially important in the case of rare cells, since the sample may only contain one or a few copies of the rare cell, thus with small volume confinement it would not be possible to achieve high cell densities of rare cell types. It would also be important for creating communities of cells which contain rare cell types.

FIG. 9 illustrates the schematics of some embodiments for GMD-based co-incubation.

Various aspects useful for practicing this invention, in particular related to methods to making gel particles or other types of droplets/particles, are disclosed in: Ho et al., 2008, *Langmuir* 24: 5663-5666 (fabrication of Janus particles from the surfaces of electrospun polymer fibers); Jiang et al., 2008, *Industr. Eng. Chem. Res.* 47: 2495-2501 (fabrication of polysaccharide-inorganic hybrid biocapsules with improved catalytic activity and stability); Laulia et al., 2008, *Small* 4: 69-76 (stretched cavity-assisted molding of micrometer and submicrometer photopolymerized hydrogel particles); Liu et al., 2008, *Int. J. Pharmaceutics* 351: 104-112 (fabrication of core-shell hybrid alginate hydrogel beads); Walther et al., 2008, *Angewandte Chemie-International Edition* 47: 711-714 (emulsion polymerization using Janus particles as stabilizers); Jang et al., 2007, *Angewandte Chemie-International Edition* 46: 9027-9031 (three-dimensional structures in a microfluidic device; stop-flow interference lithography); Khademhosseini and Langer, 2007, *Biomaterials* 28: 5087-5092 (microengineered hydrogels for tissue engineering); Glotzer and Solomon, 2007, *Nature Materials* 6: 557-562 (anisotropy of building blocks and their assembly into complex structures); Wang et al., 2007, *Chemphyschem* 8: 1157-1160 (facile fabrication of hybrid colloidosomes with alginate gel cores and shells of porous $CaCO_3$ microparticles); Nisisako and Torii, 2007, *Advanced Materials* 19: 1489-1493 (formation of biphasic Janus droplets in a microfabricated channel for the synthesis of shape-controlled polymer microparticles); Cheung et al., 2007, *Lab on a Chip* 7: 574-579 (direct patterning of composite biocompatible microstructures using microfluidics); Shepherd et al., 2006, *Langmuir* 22: 8618-8622 (microfluidic assembly of homogeneous and janus colloid-filled hydrogel granules); Nie et al., 2006, *J. Am. Chem. Soc.* 128: 9408-9412 (design, synthesis, and self-assembly of Janus and ternary particles generated by microfluidic synthesis); Dendukuri et al., 2006, *Nature Materials* 5: 365-369 (continuous-flow lithography for high-throughput microparticle synthesis); Fialkowski et al., 2005, *Nature Materials* 4: 93-97 (self-assembly of polymeric microspheres of complex internal structures); Zengler et al., 2002, *Proc. Natl. Acad. Sci. USA* 99: 15681-15686 (encapsulation of cells in GMDs for parallel microbial cultivation under low nutrient flux conditions), all of which are incorporated herein by reference.

The devices and methods of the present invention find a variety of uses. Non-limiting examples of applications include: 1) co-incubating sets of microbes that cannot be cultured independently (either obligate symbiosis or the culturing conditions have not yet been determined) (and in this way determine the functions of these microbes that cannot be grown in pure (single species) culture); 2) co-incubating sets of microbes to perform a community function (a function which does not occur when individual species are cultured); 3) community functions include: multi-step degradations (such as cellulose/complex saccharides, environmental pollutants, waste materials such as plastics) and multi-step synthesis in which the product of one microbe serves as the intermediate and is further chemically modified by another microbe; 4) spatially structured droplets could be used as a high throughput screening method to identify functional communities/culture species which cannot be grown in pure culture; 5) spatially structured droplets could be used to determine the interactions of microbe communities in the nature (in aquatic and soil environments as well as communities found within another organisms (such as in the roots of plants and in the digestive tract of various organisms) and also determine the response of microbe communities to changing conditions in the external environment (temperature, pH, gas levels, pressure changes, chemical contaminants, changes in nutrient composition, moisture content); 6) community functions also include sets of chemicals which perform new function or have increased function in response to being combined. An example would be two molecules that individually could not act as an antibiotic together have there individual functions combine to act as an antibiotic; 7) spatially structured gel droplets could also be used to create multispecies microbial communities that could be used to perform various tasks such as: droplet as a pill that could be ingested or injected into the body, droplets that could be used in bioprocesses (for instance a tank of the species mixed could not coexist, but a tank full of structured droplets would be able to perform communities functions on a large scale), droplets could be used for bioremediation (for instance droplets containing microbial communities could be added to the soil, aquatic environments, waste treatment for functions such as absorbing/decomposing contaminants, increasing nutrient flux (such as nitrogen, phosphorous, trace elements, or dissolved carbon sources), reduce the population of another organism); 8) it should be noted that because some such communities require local interactions (communities members communicate through local gradients) then communities may not be scalable, in the sense that if the community were cultured on a larger droplet or in a large tank divided into two compartments it may not work because some only the microbes near the interface (i.e., physically close to other community members) would be active. Some of these applications are discussed in greater detail below.

The devices and methods of the present invention can be used to investigate interactions between killer bacteria (with respect to either same type of bacteria or other species). Microfluidic microbial compartments provide spatial segregation of different species or strains, allowing chemical communications between cells. Based on these devices and systems, potential strategies such as distance between different species, different stages of microbial cells, vegetative cells vs. spores, etc., can be applied. In some examples, it is possible to set up a system where the microorganisms are arrested in sporulation state and can produce factors (e.g. antibacterial) that can kill other bacteria.

The devices and methods of the present invention can be used to identify and/or combine environmentally incompatible microorganisms. These microorganisms include those isolated from multicellular hosts and natural environments, genetically engineered strains, strains evolved in a laboratory setting, as well as any combination of organisms from these groups. This can be done, e.g., in beads, where species A can be protected by species B and/or C. For example, it is possible to co-incubate two or more strains that may not be easily (or at all) found in the nature. More specifically, these microbial consortia may not be found in nature frequently and also may not be easy to handle in culture in the laboratory because those two or more strains are not compatible for coexistence owing to different environment to survive. The functional communities of aerobic and anaerobic microorganisms can be a representative example. Using the spatially structured culturing methods in a microfluidic device or GMDs, microbial communities that are environmentally incompatible to coexist but are potentially expected for novel functions can be cultured and broadly applied in the fields of bioremediations, bio-refinery technologies, bio-energy and bio-fuel, degradation processes of natural products, food/cosmetic engineering, etc. Examples of environmentally incompatible communities include culturing microbial strains with different growth rates. In the laboratory, it has not been aggressively attempted to co-incubate microbial communities with different growth rates in a well-mixed flask. This mismatched growth rate of different species or strains of microorganisms may be a big bottleneck in co-incubate of microbial communities. Under the environment that spatially segregated culture wells in the devices of the present invention, the co-incubation of microbial communities with different growth rates may be possible.

In an alternative embodiment, it may be advantageous to selectively enrich or perturb the initial source population by physical or chemical treatments. The goal is to improve the relative abundance of species that are likely to possess a desired gene or metabolic pathway. For example, a microbial sample can be subjected to a period of elevated temperature to select for thermophilic species or reduced temperature to select for psychrophiles. Other physical treatments include the addition of particles of various sizes and compositions for adherent species, agitation of liquid or semi-liquid samples, high pressure treatment, exposure to light, exposure to high-energy radiation, and the like. The population can also be exposed to an exogenous carbon source such as cellulose to enrich for species that possess cellulolytic enzymes. Other chemical treatments include changes in mineral nutrients or cofactors, atmospheric composition, redox potential, osmolarity and pH. Likewise, one may add chemicals such as quorum-sensing agents, antibiotics or non-aqueous solvents. Selection can also be done crudely by creating conditions wherein some of the cells will lyse (e g, by changing the osmotic strength or adding detergents). Intact cells can be removed by centrifugation It may also be desirable in some cases to derive the genomic material from a population that has been partially cultured in a laboratory microcosm (e g, a Winogradsky column) to deliberately 'shape' its genetic profile through complex interactions among community members.

Physical separation (e.g. fractionation and sorting) of the desired organisms by dispersion and fractionation can also be used to adjust the species composition. A useful method for obtaining genomic source material is through bioprospecting.

The simplest method for dispersing and fractionating soil bacteria is to homogenize the sample in a Waring blender and then to pellet the soil particles, plant material, protists and fungi by low-speed centrifugation. A second, high-speed centrifugation is then used to pellet the bacteria. Another type of fractionation comprises filtering the cells through porous membranes or columns of coarse particles (which can also be used to separate adherent from non-adherent species). Filtration/capture can also be accomplished by affinity or size-exclusion chromatography. Affinity capture can be coupled with magnetic bead technology to aid in removing particular cell types from the medium. Density gradient centrifugation using, for example, Percoll and sucrose can be used to separate microbial cells from other material. Species that prefer to form biofilms can also be separated out by allowing them to adhere to a solid surface, such as a modified Robbins device or flow cell, which can be removed from the medium for harvesting.

Cells can also be sorted individually using fluorescence activated cell sorting. In addition to separating classes of cells based on their light scattering properties, a FACS instrument can sort microbial cells that have been selectively labeled with one or more fluorescent dyes. Thus, cells can be sorted based on fluorescence emission wavelength and intensity by choosing the appropriate laser excitation wavelength and emission windows. Fluorescent labeling may comprise direct labeling with reactive dyes.

Microorganisms for practicing the present invention can be obtained from a variety of sources. Environments for finding organisms include, but are not limited to: geothermal and hydrothermal fields, acidic soils, sulfotara and boiling mud pots, pools, hot-springs and geysers where the enzymes are neutral to alkaline, marine actinomycetes, metazoan, endo and ectosymbionts, tropical soil, temperate soil, arid soil, compost piles, manure piles, marine sediments, freshwater sediments, water concentrates, hypersaline and super-cooled sea ice, arctic tundra, Sargasso Sea, open ocean pelagic, marine snow, microbial mats (such as whale falls, springs and hydrothermal vents), insect and nematode gut microbial communities, plant endophytes, epiphytic water samples, industrial sites and ex situ enrichments. Additionally, the enzymes may be isolated from eukaryotes, prokaryotes, myxobacteria (epothilone), air, water, sediment, soil or rock, a plant sample, a food sample, a gut sample, a salivary sample, a blood sample, a sweat sample, a urine sample, a spinal fluid sample, a tissue sample, a vaginal swab, a stool sample, an amniotic fluid sample and/or a buccal mouthwash sample. The invention provides a universal and novel method that provides access to immense reservoirs of untapped microbial diversity. The invention provides the ability to grow and study these organisms. It revolutionizes our understanding of microbial physiology and metabolic adaptation and provides new sources of novel microbial metabolites. The invention can be applied to samples from several different environments, including seawater, sediments, and soil. As well, the invention provides methods to identify and modify enzymatic pathways useful for chemical, pharmaceutical, textile, food and feed, detergent, etc. applications. Various aspects of methods similar to those discussed above are disclosed in PCT Patent Applications Pub. Nos. WO05010169A2 WO0229101A2, both which are herein incorporated by reference The devices and methods of the present invention can be used to screen for and identify compounds that microorganisms are capable of producing, and that have not been identified using standard microbe cultivation techniques. Small changes in culturing conditions (for example, media composition, aeration, culture vessel, addition of enzyme inhibitors) drastically change the metabolites that are released from a cell. One strain may be producing many compounds. Even though it is possible to culture a microorganism, e.g. the bacterial strain *B. subtilis*, and even though a fair amount is known about its genome, some useful compounds that it is capable of releasing may be missed simply because the organism has never been controllably grown under particular environmental conditions and/or with particular inducers. Therefore, using hybrid-like approaches it is possible to probe a larger range of metabolite/released compounds/drug leads simply by running high throughput screens of various media conditions/additives. Some aspects of the possible ways to explore chemical diversity are disclosed in Bode et al., 2002, *ChemBioChem* 3: 619-627.

Implementation of the screenings can be done in the following ways: 1) take a known organism and screen many media and culturing conditions (vary ion concentrations, known autoinducers, amount of confinement, temperature, pH, protein additives, reaction oxygen species, stress inducers, change carbon source and concentration of carbon source, change nitrogen source and concentration of nitrogen source, change availability of various trace metals (Mn, Mo, Cu, Pt, etc.), add drugs known to interfere with specific cellular activities, add transport and ion channel inhibitors, small molecules involved in cellular communication, virulence activators, etc.). After using hybrid method to screen through many conditions, perform functional tests or other assays in plugs (Song et al., 2006, *Angew. Chem. Int. Ed.* 45: 7336-7356; Chen et al., 2006, *Curr. Opin. Chem. Bio.* 10: 226-231) to determine if compounds have been generated with properties of interest (such as drug targets, antibiotic compounds, ion channel inhibitors, virulence activation, virulence inhibition, degradation of various compounds, binding affinity, etc.); 2) perform the same method described in 1) except perform this type of screen with rare cells isolated from natural samples such as the soil, aquatic environments, animal digestive tract, etc.; 3) perform the same method described in 1) except perform this type of screen with cells which are uncultivable (no known conditions cause them to divide/reproduce outside of natural environment). If small volumes are used, should be able to detect activity even from a single cell without division. 4) use plug-based methods to collect the lysate or cell free supernatant from various types of cells and merge these solutions with other cells to elicit metabolite/compound production. Lysate/supernatant could be diluted during the screen (concentration screen using hybrid method). In this way, uncharacterized/unknown compounds/combinations of compounds could be screened to elicit production of useful compounds.

The devices and methods of the present invention can be used for the biosynthesis of biologically active compounds and industrial compounds including natural products, antimicrobial agents, fine chemicals, food additives, functional cosmetic materials, health-care compounds, and xenobiotics. While lots of the biologically active compounds have been chemically synthesized via combinatorial chemical synthesis, trends of the synthesis of bioactive compounds move from chemical methods to biological methods. According to the present invention, it is possible to use dominantly microorganisms, more specifically the enzyme systems, in a microbial community. This application provides for the development of a co-incubating system from different species of microorganisms. Representative examples of co-incubating systems include: 1) a simultaneous coupling of first and second species. Example: species 1 produces the substrate A, and species 2 produces the substrate B, respectively. If both substrates of A and B can autocatalytically react to each other via chemical reactions, the final compound X can be eventually produced by the co-incubate of species 1 and 2 together; 2) a linear synthetic sequence of species. Example: species 1 produces the substrate A, which molecule is transferred to species 2 when they are co-incubated. Then the substrate A is converted into the final compound X via enzymatic reactions of species 2. Example: when the substrate A is directly added into the reaction mixture, species 1 converts the substrate A into intermediate B. If the species 2 is co-incubated with species 1, then species 2 converts this intermediate B into the final product X; 3) a branched pathway. Example: when the substrate A is directly added into the reaction mixture, species 1 convert the substrate A into intermediate B. If the species 2 is co-incubated with species 1, then species 2 converts the intermediate B into the compound X or the compound Y depending on the environmental conditions (e.g. pH, temperature etc); 4) a repeated back and forth interactions. In an example for oligomer (or polymer) productions by the co-incubation of microbial communities, species 1 and 2 can show mutual interactions to make oligomer/polymer by adding a small unit molecule to the intermediate molecules. When the starting material and unit molecules are directly supplied into the microfluidic co-incubation bioreactor, species 1 can initiate to polymerize monomers to dimer, and then species 2 can help to modify the dimer intermediates to trimers. Under the same manner, both species can produce oligomer/polymer by interacting with each other continuously; 5) an induction by second species. Example: species 1 can convert the substrate A to the final product X only when the induction pressure exists. In this case, species 2, which can produce the inducing molecules for species, 1 can be co-incubated with species 1, resulting in the production of the compound X by species 1.

The devices and methods of the present invention can be used as medicinal or dietary preparations, in the form of pills or other pharmaceutical or dietary compositions. In some embodiments, pills may typically be shaped in a small rounded mass to be swallowed whole. The pills of the present invention contain one or more devices of the present invention. Thus, for example, a dieting pill can be made by incorporating into the pill a co-incubated community of microorganisms that can consume nutrients. Variations may include incorporating into the pill a co-incubated community of microorganisms that can degrade foods more completely, for example by increased cellulose degradation. A variety of carriers and additives may be used in the pill as well. The pill may have permeable or semipermeable walls. A subject can consume this pill pre, during, and/or post-food consumption. The pill may be made of a size that is large enough to accommodate one or more devices or droplets of the present invention, yet small enough so that so that it freely passes through a subject's intestines. Alternatively, the pill may be removed by the natural digestive processes in the intestine. As well, the pill may be made by making the community-containing devices magnetic, and then swallowing a magnet that would attract and remove all of them. This may extend the duration of activity of the pill's components. Such pills may be suitable for dieting purposes, as well for improved food digestion.

EXAMPLES

Methods. The microfluidic device was fabricated by using multilayer soft lithography in polydimethylsiloxane (PDMS) (Anderson et al., 2000, *Analytical Chemistry* 72: 3158-3164). The culture wells and the communication channel were separated by a 0.2 µm polycarbonate membrane and bonded together by using PDMS pre-polymer (Chueh et al., 2007, *Analytical Chemistry* 79: 3504-3508).

To make 2-sided GMDs cell cultures of *Escherichia coli* DsRed and *Bacillus cereus* GFP were grown in Luria-Bertani (Miller formulation, BD) at 37° C., 160 rpm overnight. Liquid agarose was made by adding 4 wt % Type IX Agarose (Sigma) to Luria-Bertani broth and melted in a 65° C. oven for one hour. One-mL aliquots of liquid agarose were cooled to 37° C. and inoculated with 100 µL of cell culture. The warm agarose with cells was then loaded into Teflon tubing connected to a Hamilton Gastight syringe backfilled with fluorinated oil FC40. The Teflon tubing containing the warm agarose was placed over a hot plate set to 45° C. to prevent the agarose from forming a gel before plug formation. Plugs were formed in a PDMS device with two aqueous inlets and a carrier fluid inlet, using a standard PDMS plug making device, similar to devices used for protein crystallization applications (Li et al., 2006, *Proc. Natl. Acad. Sci. USA* 103: 19243-19248.). Carrier fluid was the fluorinated oil FC40. Plugs were formed by flowing the warm agarose streams at 2 µL/min and flowing the carrier fluid at 10 µL/min. Plugs were collected in a 200 µm ID Teflon tubing and briefly passed over a chilling plate set to 1° C. to solidify the gel. Gel plugs were incubated in the Teflon tubing by immersing the tubing in Luria-Bertani broth and placing in a 30° C. oven overnight. Plugs were imaged after incubation using an IRE2 microscope (Leica) with a 10×0.3 NA objective and a 0.5× camera coupler. Fluorescent images were acquired with a Texas red filter set (TX2) with a 100 ms exposure time or a GFP filter set (L5) with a 100 ms exposure time. GFP and Texas Red images were overlayed using Metamorph software.

Bacterial strains of *Azotobacter vinelandii* (Av, ATCC 12837), *Bacillus licheniformis* (Bl, ATCC 25972), and *Paenibacillus curdlanolyticus* (Pc, ATCC 51899) at exponential phase were individually inoculated into individual culture wells in the microfluidic device at a concentration ~500-1000 live cells/well. The number of live cells loaded into each well varied by ±10%. The inoculated device was placed over a droplet of appropriate media on a siliconized glass cover slide, and the media filled the communication channel below the wells. The device was inverted and incubated at 30° C. The low nutrient-antibiotic media (CP media) contained carboxymethyl cellulose (1 g/L) as a sole carbon source, no nitrogen source, and penicillin G (100 µg/L). The high-nutrient media was TSB/1771 in a 4:1 (v/v) ratio. The number of viable cells in macro-scale cultures was estimated by agar plate counting, whereas the number of live cells in a microfluidic device was manually counted after the live/dead staining with solutions of SYTO9 (live) and propidium iodide (dead) (Molecular Probes).

Images of bacteria stained with live/dead dye were acquired by using an epi-fluorescence microscope (Leica) with either GFP (L5) or Texas red (TX2) filter sets, respectively. The GFP and Texas red images with the same background levels and exposure times were overlaid by using MetaMorph image software (Molecular Devices).

Mathematical modeling was performed by using Mathematica (Wolfram Research, Champaign, Ill.).

Statistical analysis was performed by using 2-way ANOVA with standard weighted-means analysis, where independent variables were time and community composition. P-values indicate the combined comparison of both variables. All error bars indicate standard errors.

Co-incubation of bacteria. A synthetic community (syntrophic in this case) was constructed by using three soil bacteria, *Azotobacter vinelandii* (Av), *Bacillus licheniformis* (Bl), and *Paenibacillus curdlanolyticus* (Pc). This community was designed to survive under nutrient-limited conditions by reciprocal syntrophy, where each species performs a unique function required for the survival of the community (FIG. 3a). In this community, only Av supplies nitrogen sources by fixing gaseous nitrogen into amino acids with a molybdenum-coupled nitrogenase under aerobic conditions, only Bl reduces antibiotic pressure by degrading penicillin G with β-lactamases, and only Pc provides a carbon energy source, such as glucose, by using cellulases to cleave carboxymethyl-cellulose.

Initial attempts were conducted to co-incubate all three species of the community under well-mixed conditions in a test tube in either nutrient-rich or nutrient-poor media (FIG. 3b). Here, the nutrient-poor media was cellulose/penicillin media (CP), which contained the β-lactam antibiotic penicillin G as the antibiotic pressure, only carboxymethyl cellulose (CM) as the carbon source, and N2 from the atmosphere as the nitrogen source. Av, Bl, and Pc cannot maintain viability over time when cultured individually in CP media. In this co-incubation, the community was unstable regardless of nutrient availability (FIG. 3b). In nutrient-rich media, the population size of Bl rapidly increased, while the population sizes of Av and Pc rapidly decreased below the limit of detection. In CP media, the population size of Av increased, while the population sizes of Bl and Pc decreased. Control experiments demonstrated that Bl grew faster in nutrient-rich media, whereas Av grew faster in nutrient-poor media and showed the highest substrate affinity. In addition, neither the presence of heat-killed Bl nor the degradation products of penicillin G had a critical effect on the viability of Av or Pc cells. These results indicate that, although the community has the potential for reciprocal syntrophic interactions, this potential is not realized under well-mixed culture conditions.

Space influences interactions between groups of bacteria. To test whether the community is stabilized by spatial structure, a microfluidic device was used that localized each bacterial species into an individual culture well separated from a microfluidic communication channel by a nano-porous membrane. This device spatially localized each species while allowing chemical communication among the species. Control experiments indicated that the bacteria remain confined and that chemicals were exchanged by diffusion through the communication channel. The device supported growth of all three species when Av, Bl, and Pc were separated into individual culture wells of the same device and cultured in nutrient-rich media.

Figure 5A:
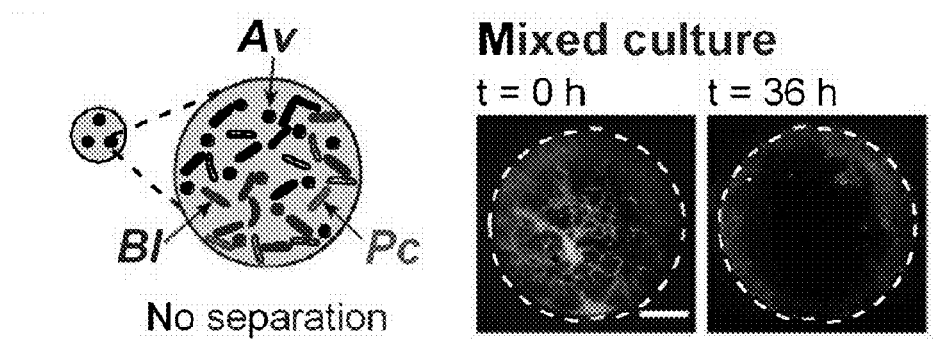
FIG. 5 shows a schematic drawing and microscopic images (a) and a graph (b) that illustrate the concept of how a synthetic microbial community only coexists at intermediate separations.
Figure 5B:
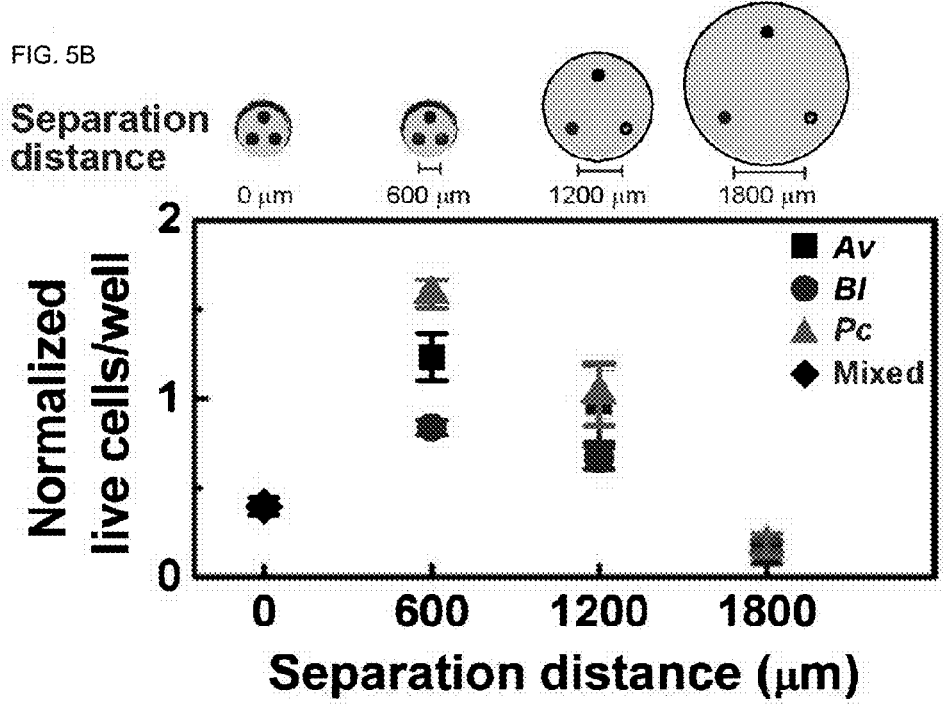
Figure 9A:
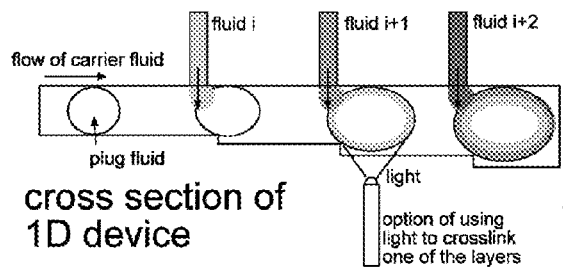
FIG. 9 is a schematic drawing that illustrates embodiments of the methods of encapsulation a plurality of microbial cells.
Figure 9B:
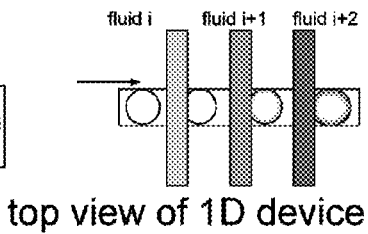
Figure 9C:
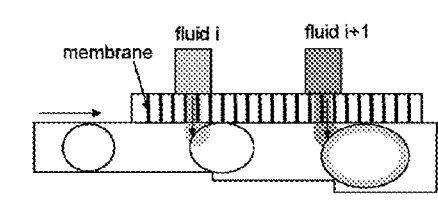
Figure 9D:
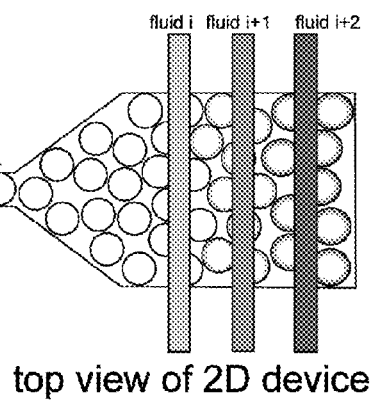
Figure 9E:
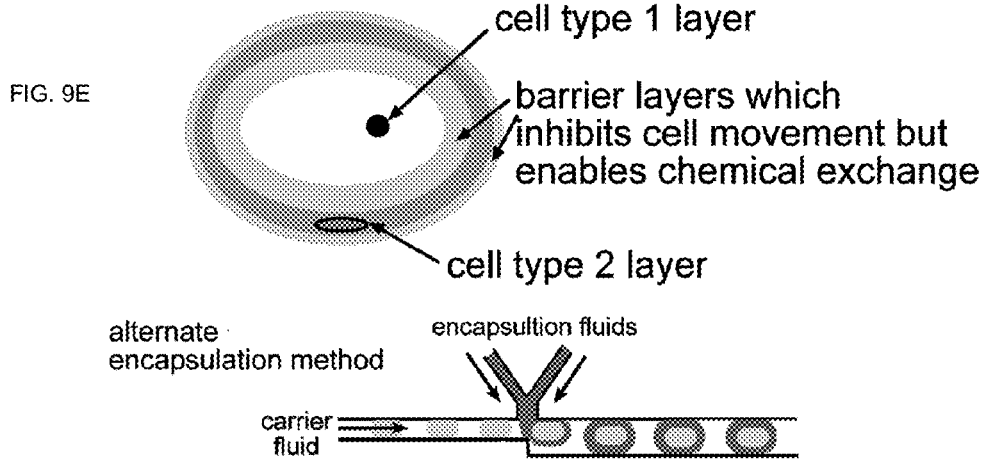
Figure 9F:

To test the influence of changes in spatial structure on this stability, the distance between the individual culture wells of the microfluidic device was varied, and the diameter of the communication channel between the wells was proportionally changed (FIG. 5). When all wells were inoculated with a mixture of all three species, effectively reducing the separation distance between species to a few micrometers, the community experienced a significant, overall population decline in 36 h (FIG. 5a). Pc could not be reliably differentiated from Av, but there was no Pc in the mixture after 36 h. A similar decline was observed when each species was individually inoculated into a culture well separated from the other wells by 1800 µm (FIG. 5b). As well, similar results were obtained when only two members of the community were cultured in the microfluidic device, where live cell numbers in cultures of two-member community were significantly less than those in cultures of all three community members. The community stably coexisted only at intermediate separation distances of the order of a few hundreds of micrometers (FIG. 5b). These results suggest that a specific spatial structure is required for the stability of the community.

FIG. 4 illustrates how the stability of the community requires communication among the three species. Fluorescence images of each species cultured in an individual culture well of the microfluidic device with either all three species in individual culture wells or the same species occupying all three culture wells were taken. Bacteria were stained with a fluorescent dye to indicate live (green in original) and dead (red in original) cells. Figure shows graphs comparing the number of live bacteria over time in a device containing all three species in individual wells (circle) or in a device containing the same species in all three wells (triangles); error bars represent standard error with N=3, except for (Av, 0 h) with N=4 and (Bl, community, 24 h), (Pc, community, 12 h), (Pc, community, 36 h), and (Pc, single species, 36 h) with N=2. P values were calculated by using two-way ANOVA.

FIG. 5 illustrates the concept of how a synthetic community only coexists at intermediate separations. FIG. 5a: a schematic drawing (left) of a mixed culture of all three species in every well of the microfluidic device and representative images (right) of a culture well containing all three species over time; bacteria were stained to indicate live (green in original) and dead (red in original) cells. Scale bar represents 50 µm. FIG. 5b: graph comparing the number of live cells of each species in devices with culture wells separated by four different distances.

Biosynthesis via co-incubation of microbial communities. It is possible to produce natural products by GMD-based co-incubation in a microfluidic device. To accomplish that, microorganisms that are involved in biosynthesis of desired natural products are used. Examples include the production of novel antibiotic derivatives by the co-incubation of two or more different species. In terms of co-incubation, species A produce the structural precursor of antibiotics, then species B modify the structure of antibiotics produced by species A by changing side chain or attaching sugars to the precursor. These synergistic reactions promote the derivatizations of precursors combinatorially. Technically, GMD and a microfluidic device may be applied together. This technique provides several advantages: i) GMD-based co-incubation via communications between species A and species B without cross-contamination; ii) physical confinement in a GMD may maintain the viability of microorganisms; iii) shorter culture time and smaller volume. Some examples of synthesis of natural products are listed below:

1) Production of novel antimicrobial agents. Example of biosynthesis system in a microfluidic device is the biosynthesis of novel antimicrobial agents by the co-incubation of different several *Streptomyces* species (Table 1). Some of species produce the hydrophobic precursor of streptomycin antibiotics, and some of other species modify the hydrophobic precursors by adding sugar moieties.

TABLE 1

*Streptomyces* species that can be used for the biosynthesis of novel antimicrobial agents by co-incubation

| Microorganisms | ATCC | Products | Comments |
| --- | --- | --- | --- |
| Streptomyces venezuelae | 15439 | Pikromycin | SV |
| Streptomyces fradiae | 19609 | Tylosin | SF |
| Saccharopolyspora erythraea | 11635 | Erythromycin | SE |
| Streptomyces antibioticus | 11891 | Oleandomycin | SA |
| Streptomyces peucetius | 29050 | Daunorubicin | SP |
| Bacillus subtilis | 6051 | | BS (test organism) |

2) Electricity-producing bacterial communities. Examples of biofuel cells that select for microbial consortia that self-mediate electron transfer have been identified by two methods (based on either the occurrence of a dominant band in a denaturing gradient gel electrophoresis pattern or on plating), and these are disclosed in Rabaey et al., 2004, *Appl. Environ. Microbiol.* 70: 5373-5382. Thus, some communities of microbes may have the ability to generate electricity in fuel cells. The strains shown in Table 2 could be used as a starting point to identify active combinations of co-incubated microorganisms. Since the methods of the present invention have the ability to create communities and control spatial structure, one could conceivably screen various combinations in various structures in order to optimize fuel cell performance.

TABLE 2

Overview of bacterial species that may have the ability to generate electricity in fuel cells (from Rabaey et al., 2004)

| Band or isolate | Accession no. | Highest homology (accession no.) | % Similarity | No. of identical base pairs | Taxon |
|---|---|---|---|---|---|
| Bands | | | | | |
| 2 | AY483162 | *Eubacterium aggregans* (AF073898) | 96 | 114/118[a] | Firmicutes |
| 3 | AY483163 | *Lactococcus lactis* subsp. *lactis* (AF515226) | 100 | 160/160 | Firmicutes |
| 4 | AY483164 | *Pseudomonas* sp. strain ARDRA PSI (AY364085) | 99 | 129/130 | Gammaproteobacteria |
| 5 | AY483165 | *Enterococcus gallinarum* CECT9707T (AJ420805) | 100 | 153/153 | Firmicutes |
| 6 | AY483166 | *Alcaligenes* sp. strain 2-6 (AY296717) | 100 | 158/158 | Betaproteobacteria |
| 7 | AY483167 | Uncultured bacterium clone up. 2 (AY212541) | 95 | 97/102 | Bacteria |
| 8 | AY483168 | Swine manure pit bacterium PPC89 (AF445290) | 98 | 69/70 | Bacteria |
| 9 | AY483169 | Uncultured earthworm intestine bacterium (AY154530) | 97 | 144/147 | Bacteria |
| 11 | AY483170 | *Lactobacillus casei* YDT21 (AF375931) | 94 | 145/153 | Firmicutes |
| 12 | AY483171 | *Clostridium* sp. strain MDA2315 (AY238334) | 100 | 127/127 | Firmicutes |
| 13 | AY483172 | Uncultured *Enterococcus* sp. clone T8-20 (AF526922) | 100 | 158/158 | Firmicutes |
| Isolates | | | | | |
| KRP1 | AY483173 | *Pseudomonas aeruginosa* ATCC 27853 (AY268175) | 95 | 189/197 | Gammaproteobacteria |
| KRP3 | AY483173 | *Pseudomonas aeruginosa* ATCC 27853 (AY268175) | 95 | 189/197 | Gammaproteobacteria |
| KRP4 | AY483174 | *Bacillus* sp. strain A24 (AF397399) | 100 | 693/693 | Firmicutes |
| KRA1 | AY483175 | *Alcaligenes faecalis* (AF155147) | 98 | 696/704 | Betaproteobacteria |
| KRA3 | AY489118 | *Enterococcus* sp. strain CDC PNS-E2 (AY321376) | 99 | 1,101/1,102 | Firmicutes |

TABLE 2-continued

Overview of bacterial species that may have the ability to generate electricity in fuel cells (from Rabaey et al., 2004)

| Band or isolate | Accession no. | Highest homology (accession no.) | % Similarity | No. of identical base pairs | Taxon |
|---|---|---|---|---|---|
| KRA4 | AY489119 | Bacillus cereus ATCC14579 (AF290547) | 100 | 1,101/1,101 | Firmicutes |
| KRA5 | AY489119 | Bacillus cereus ATCC14579 (AF290547) | 100 | 1,059/1,059 | Firmicutes |
| KRAN1 | AY489118 | Enterococcus sp. strain CDC PNS-E2 (AY321376) | 99 | 1,101/1,102 | Firmicutes |
| KRAN2 | AY483175 | Alcaligenes faecalis (AF155147) | 98 | 696/704 | Betaproteobacteria |
| KRAN3 | AY489118 | Enterococcus sp. strain CDC PNS-E2 (AY321376) | 99 | 1,101/1,102 | Firmicutes |
| KRISO1 | AY483176 | Ochrobactrum sp. strain LMG 20570 (AY040351) | 98 | 664/673 | Alphaproteobacteria |

3) Biosynthesis of various antibiotics by different stimulations. For example, *Streptomyces tenjimariensis* produces different kinds of antibiotics by the stimulation of other bacterial species when they are co-incubated (Slattery et al., 2001, *Microbial Ecology* 41: 90-96). This information can be used as a starting point for the identification of novel antibiotics that are produced *Streptomyces tenjimariensis*. Of course, similar assays could be performed using other microorganisms as starting points.

4) Biosynthesis of poly-beta-hydroxybutyrate (PHB) via bacterial community. For example, it is possible to use combinations of various microorganisms, e.g. six cyanobacteria (*Microcoleus chthonoplastes, Lyngbya aestuarii, Leptolyngbya* sp., *Oscillatoria* sp., *Geitlerinema* sp., and *Gloeocapsa* sp.), one phototrophic, anoxygenic bacteria (*Chloroflexus* sp.), and several heterotrophic bacteria (Lopez-Cortes et al., 2008, *Microbial Ecology* 56: 112-120). It is possible to co-incubate microorganisms for the production of antimicrobial agents (Iwami et al., 1992, *Appl. Environ. Microbiol.* 58: 3879-3882). In another example, it is possible to form new lipoaminopeptides, acremostatins A, B, and C, by co-incubation of *Acremonium* sp. Tbp-5 and *Mycogone rosea* DSM 12973 (Degenkolb et al., 2002, *Biosci Biotechnol Biochem.* 66: 883-886).

Induction and/or stimulation of competition and selection pressure. The devices and methods of the present invention can be used for inducing and/or competition to therefore stimulate evolution of microorganisms. Since local environmental conditions within a community could be defined using microfluidic methods, this would enable the creation of a landscape of selection pressures (over the space occupied by the community, overlapping gradients of various chemical and physical environments would create a space which is highly heterogeneous). In simple terms, providing selection pressure may result in one microorganism outcompeting (even starving to death) another microorganism. Spatial heterogeneity could aid in the rate of evolution as having heterogeneity in the local environments would enable the total population of the community to maintain diversity (for instance if all of the microorganisms in the community experienced a temperature of 45° C. then all of the communities will evolve to tolerate a 45° C. temperature, therefore the population may lose communities that have adapted to survive at low temperatures). In addition, since the evolution of some functions may require multiple separate evolutionary steps, the optimal evolutionary path may be to obtain a first evolutionary change in one environment and then acquire the second evolutionary change in another environment. In some examples, gradients of food/nutrients may be applied to bacterial co-incubation in order to elicit antibiotic production/ antibiotic evolution. The separation of the microbes in the community would also maintain diversity by varying the selection pressure and reducing competitive dynamics in the system.

In some examples, providing selection pressure could be used to identify "killer microorganisms", i.e. microorganisms that kill other organisms (Cowen and Lindquist, 2005, *Science* 309: 2185-2819). Some bacteria under stress even cannibalize their siblings (González-Pastor et al., 2003, *Science* 301: 510-513). Assays for determining killer microorganisms may be direct, using a direct readout (cell death), or indirect readout (secreted molecules). Once such killer microorganism is identified, selection pressure could be created and applied on the killer microorganism, by having a second microorganism consume some of the nutrients from the first one. This could induce the killer microorganism to evolve into an even more potent killer.

Precise control of the local environment and microfluidic sorting techniques also enable the use of artificial selection schemes. In general, natural evolutionary processes rely on the ability of an adaptation of increase the fitness of the organism. In this context, fitness is the rate at which the organism reproduces and passes on there genetic material to offspring or the rate at which the organism increases the proportion of the total population with its genetic information. Artificial selection schemes can involve selection for organisms based on function of the organism, regardless of the rate at which the organism reproduces (i.e., a trait which does not influence fitness). For example, if one is trying to evolve a microbe that produces a fluorescent protein, since the fluorescence of a protein cannot be detected by the organism itself or by other organisms, it is unlikely that producing a fluorescent protein would increase the fitness of organism, so fluorescence is not a trait which would be selected for under natural selection. However, under artificial selection, the microbes can be passed through a fluorescence detecting device such as a Fluorescence Activated Cells Sorter (FACS) and the most fluorescent microbes can be separated from the non-fluorescent population of cells to pass on genetic information to the next generation. The ability to set the selection criteria (e.g., red fluorescent vs. green fluorescent, quantum efficiency of the fluorophore between 5-10%) enables the design of criteria that would optimize the rate of evolution.

In some examples, multi-functional complexes made by microbial communities can be constructed. Such a functional community can, e.g., involve degradation of pollutant polymers as well as generation of new useful materials such as renewable energy sources.

Self-sorting of microbial communities. The devices and methods of the present invention can be used for inducing self-sorting among microorganisms. Instead of using Fluorescence Activated Cells Sorter or some other active method of sorting, a passive method of sorting can be used. For example, droplets containing the microorganism of interest may get sorted based on a density, viscosity, and/or size. In this embodiment, spatially separated microorganisms are placed in/on droplets, and are then subjected to a functional screen. The function is coupled with a particular measurable reaction (chemical, physical, biological), which in essence creates a sorting mechanism. For example, changes in density, surface tension, $CO_2$ generation, surfactant generation, hydrophobicity change, electronegativity change, magnetic change, and/or size change, may be indicators of self sorting mechanisms. The droplets/plugs might be generated randomly and mixed (although compartmentalized) with many other droplets with different compositions; the sorting mechanism would allow simple identification and transfer of "good" plugs to other selection rounds. The selection round(s) can be repeated. One advantage is that one does not have to screen/measure plugs that don't perform the function of interest, test droplets self-segregate.

Self-sorting may lead to directed evolution of target functions (Wang et al., 2004, *Proc. Natl. Acad. Sci. USA* 101: 16745-16749). Therefore, the generated self-sorting systems can be used to direct the evolution of preferred functions which are related to the sorting mechanism. Self-sorting will allow for high-throughput screening of conditions (essential for efficient evolution because need high diversity in screening populations) while also imposing a (possibly adjustable) selection criteria/selection pressure (those that don't separate themselves will not go on to further optimization rounds.

Self-sorting can be performed using direct screening: for example, if one is looking for polymerization catalysts, they would make more viscous by polymerizing substrate inside. Then one could apply high shear to break up all of the drops in a bucket except the most viscous ones, and then filter out the small fragments and capture the big drops (there are also separations based on size using hydrodynamics)—or just resort only to the big ones using standard sorting techniques. Alternatively, self-sorting can be performed using indirect screening, that requires more engineering: coupling the process of interest to the process that can be easily detected if one is looking for cellulases secreted by a bacterium so they can degrade a particular form of cellulose into sugars, adding to each drop enzyme cocktail (or have it expressed in the microbes) that converts sugars to $CO_2$, and these bubbles float the "productive" drops. In a system where collecting the top $1/10^X$ droplets, where X is large is important, self-sorting takes place in a field that changes more slowly than the drops are sorted. In the limit, the field is constant as gravity or magnetism.

Self-sorting can be used to evolve chemical systems (sets of interacting chemical reactions) to perform complex functions. The devices and methods of the present invention can be used to effectively control selection pressure/criteria, control local conditions, and do high throughput screening (automated sorting tricks, generating diversity in trials). Examples of directed evolution are disclosed in: a method for rapid screening and simultaneous amplification of bacterial surface-display libraries (Patel et al., 2001, *Biochem J.* 357: 779-785); optical processing of Bacterial Libraries for directed evolution (Scruggs and Woodbury, 2003, *Biotechnology and Bioengineering* 84: 445-451); and laboratory-directed protein evolution (Yuan et al., 2005, *Microbiology and Molecular Biology Reviews* 69: 373-392)

One variant of the self-sorting method is magnetic self-sorting. Reactions with change in magnetism (any combination with any direction of changes among diamagnetism, paramagnetism, and ferromagnetism) could be used in self-sorting. Examples of reactions that produce paramagnetic solid from liquid or diamagnetic materials that can be used include (but are not restricted to): 1) $Ag^+ -> Ag:Ag^+$ has electron configuration of d10, so it is diamagnetic. Ag has electron configuration of s1d10, so it is paramagnetic. The autocatalyst is Ag (or its surface to be more detailed); 2) Guyard reaction: Mn(VII) (such as, $KMnO_4$) reacts with Mn(II) (some soluble salt such as nitrate or chloride) and makes $MnO_2$ which is a black paramagnetic powder. The autocatalyst is $MnO_2$ solid (its surface). Initially, all particles are not magnetic or are only weakly magnetic. As a result of detecting a specific molecule/function, a particle initiates a set of reactions which will create magnetic material (solid or liquid) inside or attached to the active particles. A magnetic field could then be applied to all of the particles and those which have created a magnetic material could be separate from inactive particles that have not created a magnetic material. If the amount of magnetic material created is proportional to the level of activity (more active, more magnetic) then a magnetic field could be used to measure a graded response (could detect high active, medium activity, low activity, no activity particles). Also, if a desired activity leads, directly or indirectly, to formation of a magnetic material, for example, by leading to a change in the redox state.

Screen for new compounds: This can be done in a variety of ways. One is to use methods to assemble communities of cells from soil extract. Once communities have been obtained, incubate plugs containing cells overnight. Then use the plug containing the communities as a condition. in the hybrid method: merge the gel droplet containing the community a buffer plug to extract the compounds which have been released by the community. Then use this with many, e.g. thousands of plugs, containing cells of *Streptomyces* species. After plugs containing *Streptomyces* have been merged with rare cell supernatant and incubated, screen for antibiotic production. In this way, compounds in the supernatant of the rare cell could induce the production of new antibiotic compounds. Another way is to use stochastic confinement to isolate communities of cell from ocean sediments using co-incubation in gel beads or in a spatially structure device. Once plugs containing the community have been collected, use the hybrid method to screen various media conditions such as (phosphate concentration from 0 to 100 μM, autoinducer 2 concentration from 0 to 100 μM, glucose from 0 to 10 mM). Then incubate the cells in the new media conditions. Then various functional/genetic tests can be performed in the plugs to determine which media conditions yield growth and/or production of compounds with desired properties.

Schematic explanation of synthetic communities. All of the members of species A, B, and C should depend on other members for the survival at particular conditions. For example, it can be assumed that one condition that it doesn't have essential components of I, II, and III for each community member. However, each member only can provide one of the essential components, for example species A can provide component I, but still requires B and C for its survival at particular condition. Other two species are placed in the same conditions, so they need to cooperate with each other at a particular condition for their survival. This condition can be tested by omitting one of the members in particular conditions, in which case the knock-out community cannot survive under the imposed harsh conditions.

Artificial Symbiosis Among Microbial Strains/Communities.

In an example of studying the natural symbiosis among the uncultured strains/unknown communities, a high throughput screening (HTS) for the identification of an antibiotic degrading community may be performed. If some bacterial community from natural soil sample can survive under the penicillin antibiotic condition, they will probably produce β-lactamases. Thus, the soil sample treated with cycloheximide (for growth inhibition of eukaryotes) is inoculated into a device of the present invention with various sub-geometries (A) or without any sub-geometry (B). This device is placed on the media supplemented by the penicillin G. The results are then analyzed. By comparing (A) and (B), it is possible to identify the smallest community producing β-lactamases. If the natural sample is chosen, then all strains attained from the sample should be identified.

In an example of high throughput screening (HTS) for quorum sensing (QS) community, quorum sensing bacteria and the reporter strains can be used to screen other QS strains in the sample. Based on the quorum sensing between *Pseudomonas* strain (PAO1) and reporter strain (*E. coli* LC4), it is possible to screen for new quorum sensing bacteria from soil bacteria. Thus, a QS reporter is mixed with soil bacteria and inoculated into the device of the present invention. The results are then analyzed. If luminescence is detected from several connected bacterial communities, high throughput method of screening for HSL producers is achieved.

In an example of high throughput screening for quorum quenching community, the coupled community of quorum sensing bacteria and the reporter strains can be used to screen the novel quorum quenching (QQ) strain/community in a sample (e.g. soil sample). A reporter strain is inoculated on an agar plate, and the cocktail of QS bacteria and soil bacteria is inoculated on the device by vacuum. Control experiment can be done without soil bacteria. The results are then analyzed. Potent candidates of quorum quenching bacteria can be identified in the non-luminescent region.

In an example of high throughput screening for a co-incubated bacterial community, e.g. syntrophic bacterial community, syntrophic bacteria may be used. If, for example, *Symbiobacterium thermophilum* is used, then it is important to indicate the one whose growth depends on co-incubating with cognate bacteria (e.g. thermophilic *Bacillus* sp.). Syntrophic bacteria can be used to find the alternative counterpart for co-incubation or for the elucidation of syntrophy mechanism.

The syntrophic strain and the other (e.g. soil) bacteria are inoculated on the device, and a growing community is identified. The mode of syntrophism is the compensation against the lack of essential enzymes. Syntrophic model organisms are a rare find in the nature, yet they are very important with respect to microbial taxonomy, ecology, uncultivability, and genome library of microorganisms. The obtained results may help identify potent candidates of novel cognate bacteria.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters normally encountered and obvious to those skilled in the art, are within the scope of this invention. All publications, patents, and patent applications cited herein are incorporated by reference in their entirety for all purposes. Also incorporated by reference in their entirety for all purposes are the supplementary materials (including information, text, graphs, images, tables, and movies) available online, and associated with some of the above-referenced publications.

What is claimed is:

1. A method, comprising:
   (1) providing an ingestible capsule with a defined spatial structure, the ingestible capsule comprising a first compartment and a second compartment connected to the first compartment via a communication channel, wherein the first and second compartments are physically separated by a distance x;
   (2) placing a first individual type of microorganism in the first compartment;
   (3) placing a second individual type of microorganism in the second compartment, wherein the distance x both reduces competition between the first and second individual types of microorganisms and allows for exchange of information and/or substance between the first and second individual types of microorganisms; and
   (4) co-incubating the first individual type of microorganism in the first compartment and the second individual type of microorganism in the second compartment so that the first individual type of microorganism performs a function differently than it would if the second individual type of microorganism was absent.

2. The method of claim 1, wherein during the co-incubating step, the first individual type of microorganism produces an incubation product that it otherwise would not produce when the second individual type of microorganism is absent.

3. The method of claim 1, wherein during the co-incubating step, the first individual type of microorganism does not produce an incubation product that it otherwise would produce when the second individual type of microorganism is absent.

4. The method of claim 1, wherein during the co-incubating step, the first individual type of microorganism degrades or removes an external component in an amount that differs from what it would otherwise degrade when the second individual type of microorganism is absent.

5. The method of claim 1, wherein a chemical and/or biological substance is transported through the communication channels between the different individual type of microorganisms placed in the first compartment and the second compartment.

6. The method of claim 1, wherein the ingestible capsule further comprises a barrier disposed in the communication channel, wherein the barrier blocks passage of microorganisms from one compartment to another, but allows a soluble chemical and/or biological substance to pass from one compartment to another.

7. The method of claim 6, wherein the barrier is selected from a group consisting of a membrane, a gel, a nanostructure, a pore, and a structure that is not permeable to microorganisms but is permeable to the soluble chemical and/or biological substance.

8. The method of claim 1, wherein the distance x is about 25 microbe lengths, the microbe length defined by the average length of the first and second individual type of microorganisms.

9. The method of claim 1, wherein the distance x is between about 50 μm and about 500 μm.

10. The method of claim 1, wherein the first and second individual types of microorganisms are environmentally incompatible.

11. The method of claim 1, wherein the first and second individual types of microorganisms are localized in the first and second compartments, respectively.

12. The method of claim 1, wherein the second individual type of microorganism performs a function differently than it would if the first individual type of microorganism was absent.

* * * * *

UNITED STATES PATENT AND TRADEMARK OFFICE
CERTIFICATE OF CORRECTION

PATENT NO. : 9,090,885 B2
APPLICATION NO. : 12/670725
DATED : July 28, 2015
INVENTOR(S) : James Q. Boedicker, Rustem F. Ismagilov and Hyun Jung Kim Page 1 of 1

It is certified that error appears in the above-identified patent and that said Letters Patent is hereby corrected as shown below:

In the specification

In column 1, lines 16-20, change

This invention was made with United States government support under grant number 1 DP1 0D003584-01 awarded by the NIH Director's Pioneer Award program, part of the NIH Roadmap for Medical Research. The United States government has certain rights in this invention.

to

This invention was made with government support under Grant No. OD003584 awarded by the National Institutes of Health. The government has certain rights in this invention.

Signed and Sealed this
Ninth Day of August, 2016

Michelle K. Lee
*Director of the United States Patent and Trademark Office*